US012214158B2

(12) United States Patent
Peterson et al.

(10) Patent No.: US 12,214,158 B2
(45) Date of Patent: Feb. 4, 2025

(54) SYSTEMS AND METHODS FOR SYRINGE HANDLING

(71) Applicant: Smiths Medical ASD, Inc., Plymouth, MN (US)

(72) Inventors: Benjamin Peterson, Apple Valley, MN (US); Walter Dobrovolny, Saint Paul, MN (US); Jonathan Sanborn, Saint Louis Park, MN (US); Henry Madden, Minneapolis, MN (US); Steven Plager, Eden Prairie, MN (US); Christopher Lacy, Arden Hills, MN (US); Kevin Krautbauer, Saint Paul, MN (US); Dennis Babcock, Maple Grove, MN (US); Dean Sibik, Harris, MN (US); Benn Horrisberger, Blaine, MN (US); Grant Adams, Anoka, MN (US); Seth Schulte, Saint Paul, MN (US)

(73) Assignee: Smiths Medical ASD, Inc., Plymouth, MN (US)

( * ) Notice: Subject to any disclaimer, the term of this patent is extended or adjusted under 35 U.S.C. 154(b) by 1133 days.

(21) Appl. No.: 17/250,010

(22) PCT Filed: May 3, 2019

(86) PCT No.: PCT/US2019/030565
§ 371 (c)(1),
(2) Date: Oct. 30, 2020

(87) PCT Pub. No.: WO2019/213496
PCT Pub. Date: Nov. 7, 2019

(65) Prior Publication Data
US 2021/0236719 A1    Aug. 5, 2021

Related U.S. Application Data

(60) Provisional application No. 62/666,413, filed on May 3, 2018.

(51) Int. Cl.
*A61M 5/145* (2006.01)

(52) U.S. Cl.
CPC ... *A61M 5/1452* (2013.01); *A61M 2205/8206* (2013.01)

(58) Field of Classification Search
CPC .............. A61M 5/1452; A61M 5/1456; A61M 5/1458; A61M 5/1408; A61M 2205/8206
See application file for complete search history.

(56) References Cited

U.S. PATENT DOCUMENTS

| 4,424,720 A | 1/1984 | Bucchianeri |
| 5,295,966 A | 3/1994 | Stern et al. |

(Continued)

FOREIGN PATENT DOCUMENTS

| EP | 1186311 B1 | 11/2004 | |
| EP | 1679091 A2 * | 7/2006 | .......... A61M 5/1456 |

(Continued)

OTHER PUBLICATIONS

International Search Report and Written Opinion for International Application No. PCT/US2019/030565 mailed Jul. 15, 2019.

(Continued)

*Primary Examiner* — Laura A Bouchelle
*Assistant Examiner* — Sarah Dympna Grasmeder
(74) *Attorney, Agent, or Firm* — Husch Blackwell LLP

(57) ABSTRACT

A syringe pump configured to at least partially surround a syringe loaded into the pump. The syringe pump including a syringe pump housing defining a syringe receptacle shaped and sized to accept loading of the syringe, a plunger driver assembly configured to manipulate a plunger of a syringe loaded into the syringe pump, and a syringe housing including a syringe barrel shield pivotably coupled to the syringe pump housing configured to at least partially enclose a syringe loaded into the syringe pump within the syringe (Continued)

receptacle, and a syringe plunger tray and lid assembly operably coupled to the syringe pump housing and configured to at least partially enclose a portion of the plunger driver assembly.

10 Claims, 22 Drawing Sheets

(56) References Cited

U.S. PATENT DOCUMENTS

| | | |
|---|---|---|
| 5,533,981 A | 7/1996 | Mandro et al. |
| 5,545,140 A | 8/1996 | Conero et al. |
| 5,814,015 A | 9/1998 | Gargano et al. |
| 5,879,360 A | 3/1999 | Crankshaw |
| 5,954,697 A * | 9/1999 | Srisathapat ......... A61M 5/1456 604/154 |
| 6,019,745 A | 2/2000 | Gray |
| 6,305,908 B1 * | 10/2001 | Hermann ......... A61M 5/14244 417/234 |
| 6,500,151 B1 | 12/2002 | Cobb et al. |
| 6,519,569 B1 | 2/2003 | White et al. |
| 6,551,277 B1 | 4/2003 | Ford |
| 6,592,551 B1 | 7/2003 | Cobb |
| 6,656,148 B2 | 12/2003 | Das et al. |
| 6,743,202 B2 | 6/2004 | Hirschman et al. |
| 6,966,895 B2 | 11/2005 | Tribe |
| 7,161,488 B2 | 1/2007 | Frasch |
| 7,236,936 B2 | 6/2007 | White et al. |
| 7,422,570 B2 | 9/2008 | Gerlach et al. |
| 7,635,349 B2 | 12/2009 | Tribe et al. |
| 7,859,473 B2 | 12/2010 | Gibson |
| 8,161,810 B2 | 4/2012 | Cadieux et al. |
| 8,182,461 B2 | 5/2012 | Pope et al. |
| 8,715,224 B2 | 5/2014 | Kamen et al. |
| 8,834,443 B2 | 9/2014 | Yeung |
| 8,876,793 B2 | 11/2014 | Ledford et al. |
| 8,911,403 B2 | 12/2014 | Flachbart et al. |
| 9,114,213 B2 | 8/2015 | Murakami et al. |
| 9,155,835 B2 | 10/2015 | Watanabe et al. |
| 9,265,890 B2 | 2/2016 | Chattaraj et al. |
| 9,295,778 B2 | 3/2016 | Kamen et al. |
| 9,352,083 B2 | 5/2016 | Heitmeiter et al. |
| 9,427,521 B2 | 8/2016 | Pope et al. |
| 9,623,180 B2 | 4/2017 | Iio et al. |
| 9,744,304 B2 | 8/2017 | Swift et al. |
| 9,753,015 B2 | 9/2017 | Bardina et al. |
| D803,386 S | 11/2017 | Sabin et al. |
| D803,387 S | 11/2017 | Bodwell et al. |
| 9,861,740 B2 | 1/2018 | Adams |
| 9,895,488 B2 | 2/2018 | Morton |
| 9,976,551 B2 | 5/2018 | Blomquist |
| 10,004,847 B2 | 6/2018 | Wander et al. |
| D828,547 S | 9/2018 | Lacy et al. |
| 10,076,608 B2 | 9/2018 | Dowden et al. |
| D846,735 S | 4/2019 | Sanborn et al. |
| 2004/0220526 A1 | 11/2004 | Boyne-Aitken |
| 2007/0074596 A1 | 4/2007 | Siefert |
| 2012/0215170 A1 | 8/2012 | Traversaz et al. |
| 2013/0245599 A1 | 9/2013 | Williams et al. |
| 2014/0188076 A1 | 7/2014 | Kamen et al. |
| 2015/0133890 A1 | 5/2015 | Wander et al. |
| 2015/0297832 A1 | 10/2015 | Blomquist |
| 2017/0203032 A1 | 7/2017 | Dowden et al. |
| 2017/0258985 A1 | 9/2017 | Adams et al. |
| 2020/0129691 A1 | 4/2020 | Lacy et al. |
| 2020/0171244 A1 * | 6/2020 | Weikart .............. C23C 16/5093 |

FOREIGN PATENT DOCUMENTS

| | | |
|---|---|---|
| EP | 1679091 B1 | 1/2011 |
| EP | 2260891 B1 | 3/2018 |
| JP | 2001178821 | 7/2001 |
| JP | 4674689 B2 | 4/2011 |
| JP | 4805724 B2 | 11/2011 |
| JP | 4833732 B2 | 12/2011 |
| JP | 5457365 B2 | 4/2014 |
| JP | 2018047320 | 3/2018 |
| WO | WO 2016/014335 A1 | 1/2016 |
| WO | 2016099891 | 6/2016 |
| WO | WO 2016/183342 A1 | 11/2016 |
| WO | 2016205584 | 12/2016 |
| WO | WO 2017/023489 A1 | 2/2017 |
| WO | WO 2017/074599 A1 | 5/2017 |
| WO | 2018046313 A1 | 3/2018 |
| WO | WO 2019/018658 A2 | 1/2019 |
| WO | WO 2019/055516 A2 | 3/2019 |

OTHER PUBLICATIONS

FMH Employees "Pediatric Pump Operation: Medfusion Syringe Pump": Published on Mar. 28, 2012; Retrieved from the Internet [Jun. 27, 2019] URL: https://www.youtube.com/watch?v=zrtDd7TxmZ4.

International Preliminary Report on Patentability for PCT Application PCT/US2019/030565, dated Nov. 3, 2020, 6 pgs.

European Search Report for Application No. 19795971.1, dated Mar. 18, 2022, 14 pages.

* cited by examiner

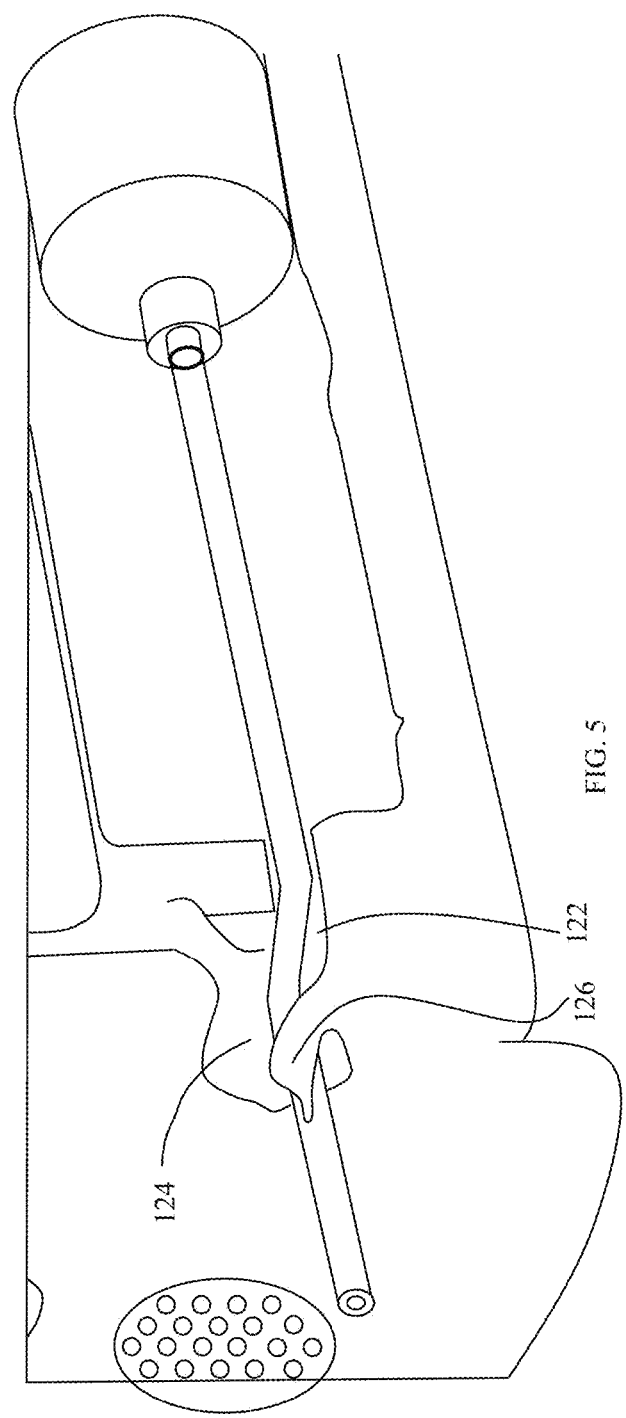

SYSTEMS AND METHODS FOR SYRINGE HANDLING

RELATED APPLICATION

The present application is a National Phase entry of PCT Application No. PCT/US2019/030565, filed May 3, 2019, which claims the benefit of U.S. Provisional Application No. 62/666,413 filed May 3, 2018, the disclosures of which are hereby incorporated by reference in their entireties.

TECHNICAL FIELD

The present disclosure relates generally to medical devices, and more particularly to systems and methods for syringe handling by infusion pumps.

BACKGROUND

In the medical arts, infusion pumps are useful in managing the delivery and dispensation of prescribed therapeutic agents, nutrients, drugs, medicaments such as antibiotics, blood clotting agents, analgesics, and other fluid and/or fluid-like substances (collectively "medicaments" or "infusates") to patients in volume- and time-controlled doses among other parameters. Medicaments can be accurately and continuously administered by such pumps, at infusion rates ranging from as low as 0.1 ml/hr to as much as 1200 ml/hr. Because of their ability to deliver medicaments in a precise, accurate, and continuous manner over an extended period of time, infusion pumps can provide some significant advantages over manual infusion techniques.

Infusion pumps are particularly useful for treating diseases and disorders that require regular pharmacological intervention, including cancer, diabetes, and vascular, neurological, and metabolic disorders. Infusion pumps also enhance the ability of healthcare providers to deliver anesthesia, manage pain and provide palliative care. Depending upon their specific designs and intended uses, infusion pumps can be used to administer infusates through various delivery methods and routes, including intravenously, intraperitoneally, enterally, intra-arterially, subcutaneously, neuraxially, and specifically into an intraoperative site, epidural space, and subarachnoid space. Infusion pumps are used in various settings, including hospitals, neonatal and pediatric intensive care units, nursing homes, and other short-term and long-term medical facilities, as well as in residential care settings. Infusion pumps can include various constructions, modes of operation, and types.

Generally, infusion pumps can include a variety of types of pumps. In some cases, these infusion pumps include syringe pumps, in which a pre-filled syringe is mechanically driven under microprocessor control to deliver a prescribed amount or dose of medicament to a patient through an infusion line or tubing in fluid connection with the syringe. Syringe pumps typically include a motor that rotates a lead screw. The lead screw in turn activates a plunger driver which forwardly pushes a plunger within a barrel of the syringe that has been removably installed in the pump. Pushing the plunger forward thus forces the infusate outwardly from the syringe, into the infusion line or tubing, and into the patient. Examples of syringe pumps are disclosed in published PCT Application WO2016/183342, titled "High Accuracy Syringe Pumps," and U.S. Published Patent Application No. 2017/0203032, titled "Method and Apparatus for Overload Protection in Medicament Syringe Pumps," both of which are hereby incorporated by reference herein. As used throughout this disclosure, the term "syringe pump" is intended to generally pertain to any device which acts on a syringe to controllably force infusates outwardly therefrom.

While various syringe pumps have been used in medical environments for many years, these devices remain rather complex medical devices with some limitations to their efficient, effective and safe use. Therefore, there is a need for syringe pumps which provide greater flexibility and ease of use to operators. Moreover, due to the vital role of infusion pumps in medical procedures and treatments, syringe pumps which provide enhanced safety to patients are needed as well.

SUMMARY OF THE DISCLOSURE

Embodiments described or otherwise contemplated herein substantially provide the advantages of improving flexibility, ease of use, operation, as well as patient safety, among other advantages.

One embodiment of the present disclosure provides a syringe pump configured to support infusion tubing attached to a syringe loaded into the pump for the purpose of inhibiting unwanted separation of the infusion tubing from the syringe during use. The syringe pump can include a syringe pump housing defining a syringe receptacle shaped and sized to accept loading of a syringe. The syringe pump housing can further define an infusion tube retention passage defined by a channel shaped and sized to force an axis of infusion tubing entering the channel in proximity to the syringe to be offset from an axis of the infusion tubing exiting the channel. The infusion tubing retention passage can further define a hook structure configured to serve as an aid in retaining a portion of the infusion tubing within the channel.

Another embodiment of the disclosure provides a syringe pump configured to inhibit unintentional delivery of medicament as a result of an external force applied to the syringe pump. The syringe pump can include a housing and a syringe plunger driver assembly. The syringe pump housing can define a syringe receptacle shaped and sized to accept loading of a syringe. The syringe plunger driver assembly can include a bumper operably coupled to an outer portion of the syringe plunger driver assembly. The bumper can be generally rounded in shape and can be fabricated of a resilient material configured to absorb external forces acting upon the plunger head assembly to inhibit unintentional delivery of medicament as a result of an external force applied to the syringe plunger driver assembly.

Another embodiment of the present disclosure provides a syringe pump configured to enable one-handed manipulation of the syringe pump during loading and unloading of a syringe into the syringe pump. The syringe pump can include a syringe pump housing and a syringe plunger driver assembly. The syringe pump housing can define a syringe receptacle shaped and sized to accept loading of a syringe. The syringe plunger driver assembly can include a trigger, a clutch assembly, and a flipper. The trigger can be positioned on an ergonomically formed plunger driver head. The clutch assembly can be configured to selectively shift from a lead screw capture position to a lead screw release position to uncouple the syringe plunger driver assembly from a motor and syringe drive components and enable the syringe plunger driver to slide relative to the syringe pump housing. The flipper can be configured to selectively rotate relative to the ergonomically formed plunger driver head from a syringe plunger capture position to a syringe plunger loading/unloading position to enable a syringe to be positioned with the syringe receptacle. Depressing or activating the trigger can simultaneously shift the clutch assembly to the lead screw release position and the flipper to the syringe plunger loading/unloading position.

Another embodiment of the present disclosure provides a syringe pump including a housing, a powertrain having a lead screw, and a clutch assembly. The clutch assembly includes first and second half-nuts, a cam having first and second lobes, the first lobe operable to move the half-nuts into engagement with the lead screw and the second lobe operable to move the half-nuts into disengagement with the lead screw, and a leaf spring in communication with at least one of the half-nuts. The syringe pump also includes a plunger driver assembly including a flipper configured to be movable between a capture position and an open position, a trigger connected to both the clutch assembly and the flipper, and a biasing element configured to bias the flipper into the capture position.

The summary above is not intended to describe each illustrated embodiment or every implementation of the present disclosure. The figures and the detailed description that follow more particularly exemplify these embodiments.

BRIEF DESCRIPTION OF THE DRAWINGS

The disclosure can be more completely understood in consideration of the following detailed description of various embodiments of the disclosure, in connection with the accompanying drawings, in which:

FIG. 5 is a close-up view depicting an infusion line retention passage of a front housing assembly, in accordance with an embodiment of the disclosure.

Figure 1:
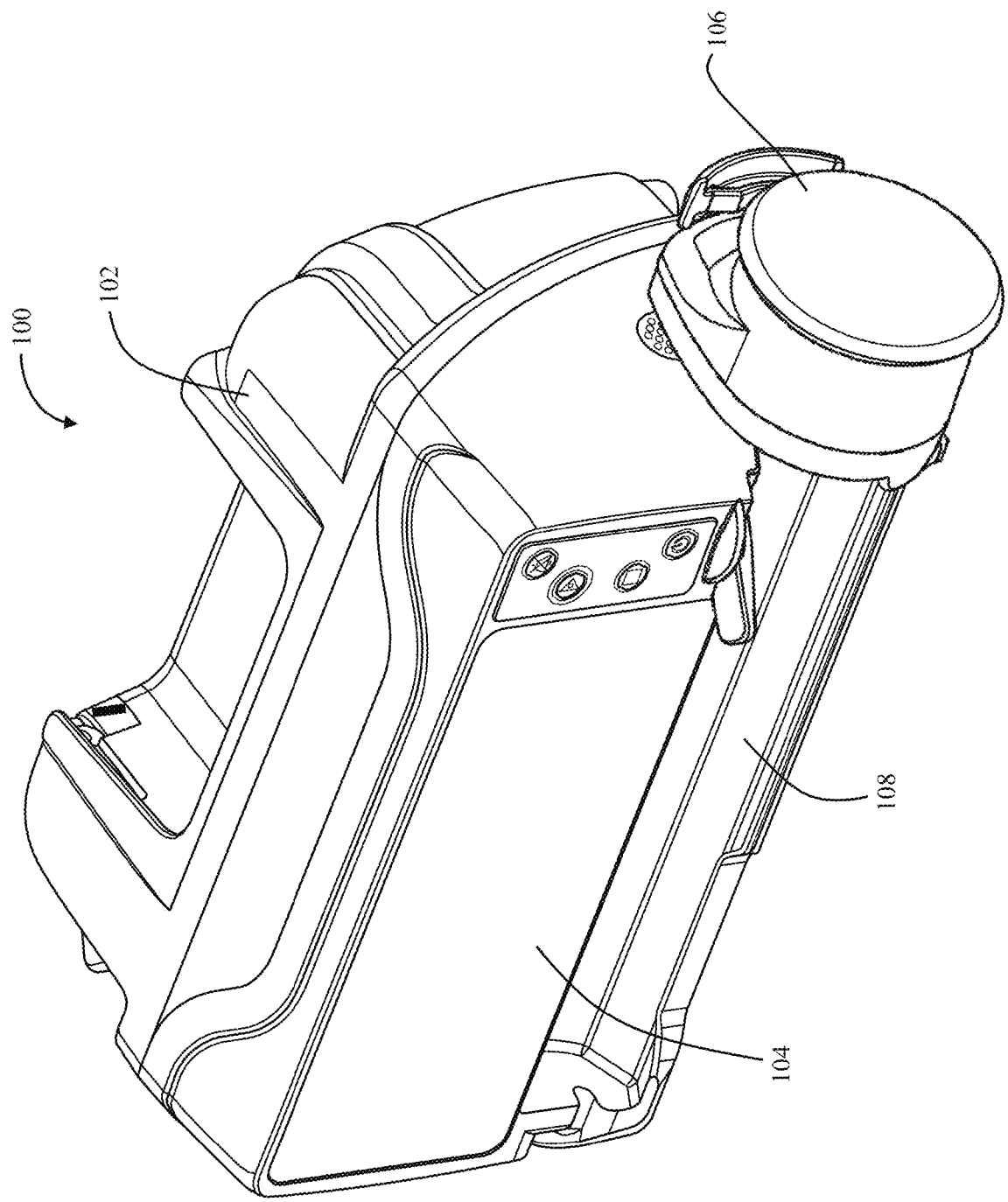
FIG. 1 is a front perspective view depicting a syringe pump, in accordance with an embodiment of the disclosure.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DETAILED DESCRIPTION

Figure 2:
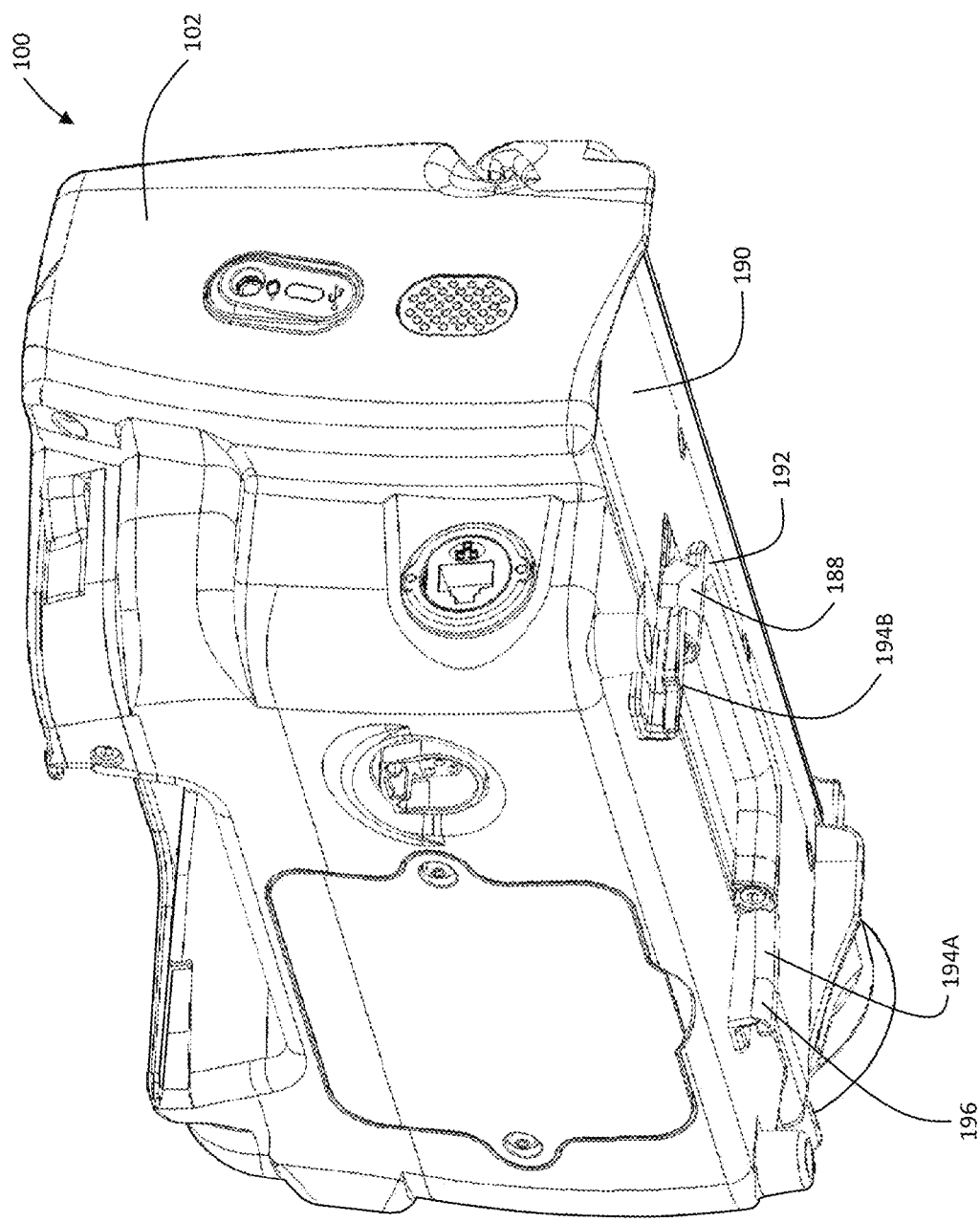
FIG. 2 is a rear perspective view depicting the syringe pump of FIG. 1.

Referring to FIGS. 1-2, perspective front and rear views of a syringe pump 100 are depicted in accordance with an embodiment of the disclosure. The syringe pump 100 can include a housing 102, user interface 104, syringe drive assembly 106, and syringe receptacle 108.

Figure 3:
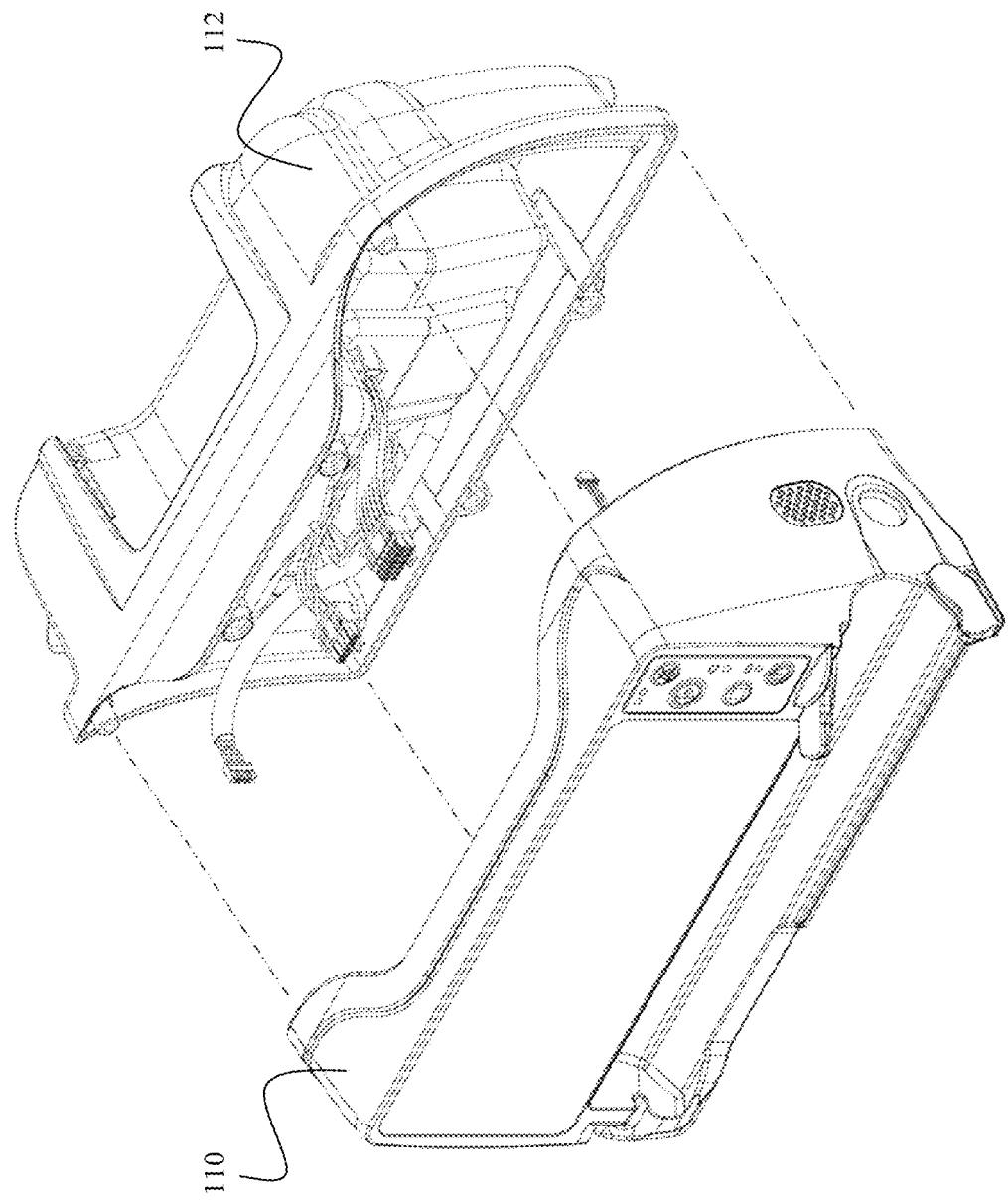
FIG. 3 is an exploded view depicting a syringe pump in accordance with an embodiment of the disclosure, in which a housing assembly and a rear housing assembly are separated from one another.
Figure 4A:
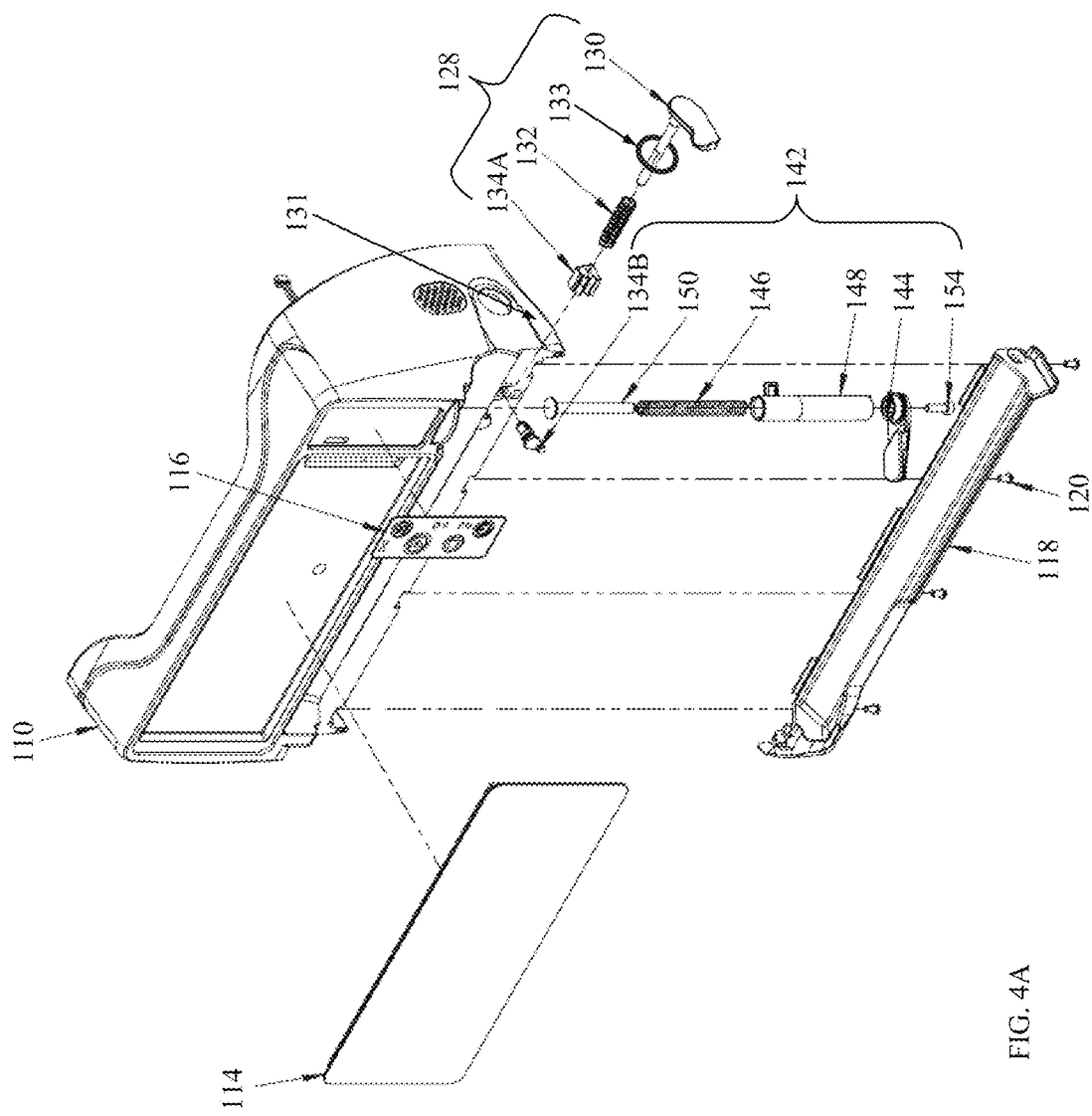
FIG. 4A is a front perspective, exploded view depicting a front housing assembly in accordance with an embodiment of the disclosure.
Figure 4B:
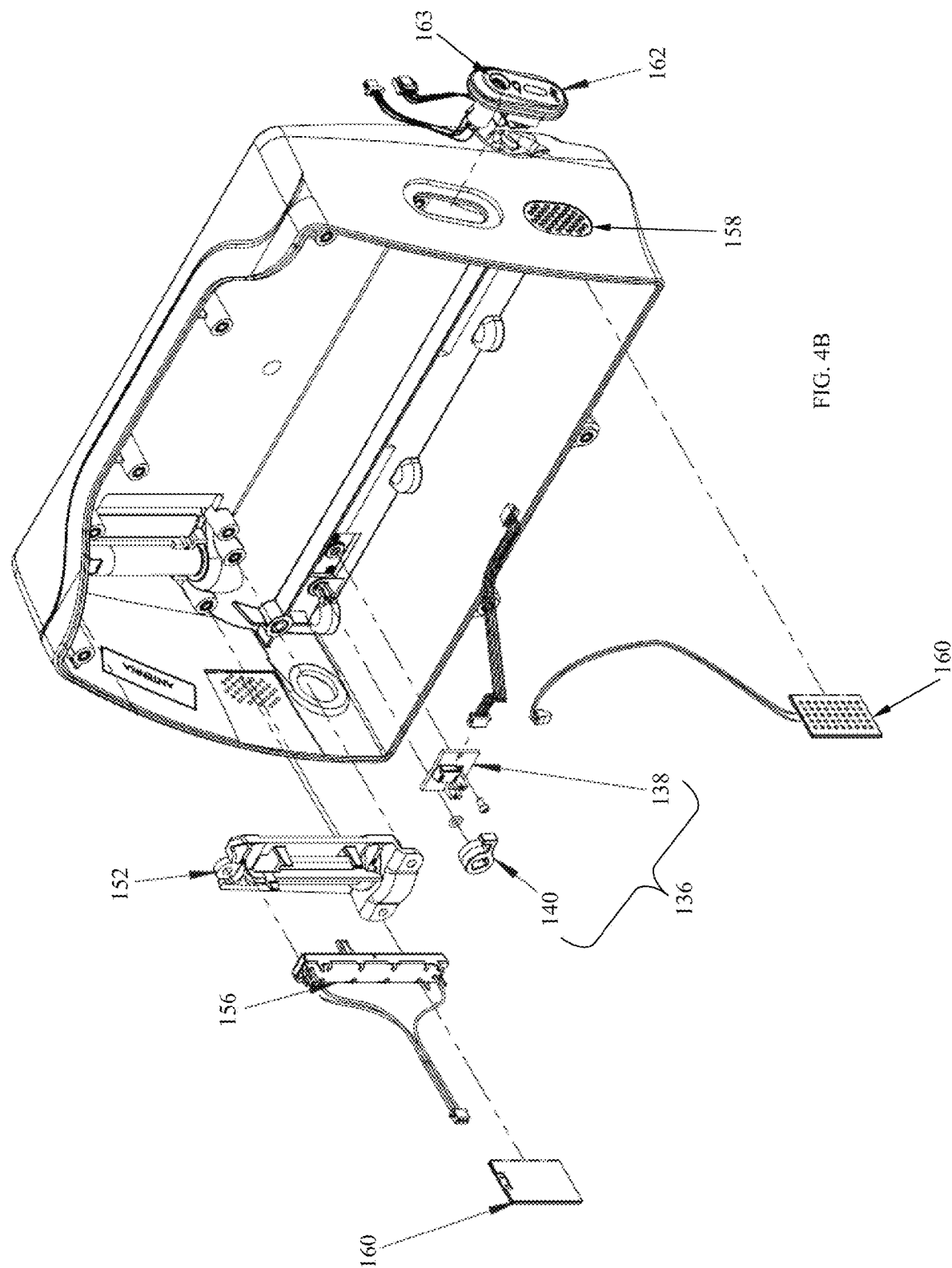
FIG. 4B is a rear perspective, exploded view depicting the front housing assembly of FIG. 4A.
Figure 6A:
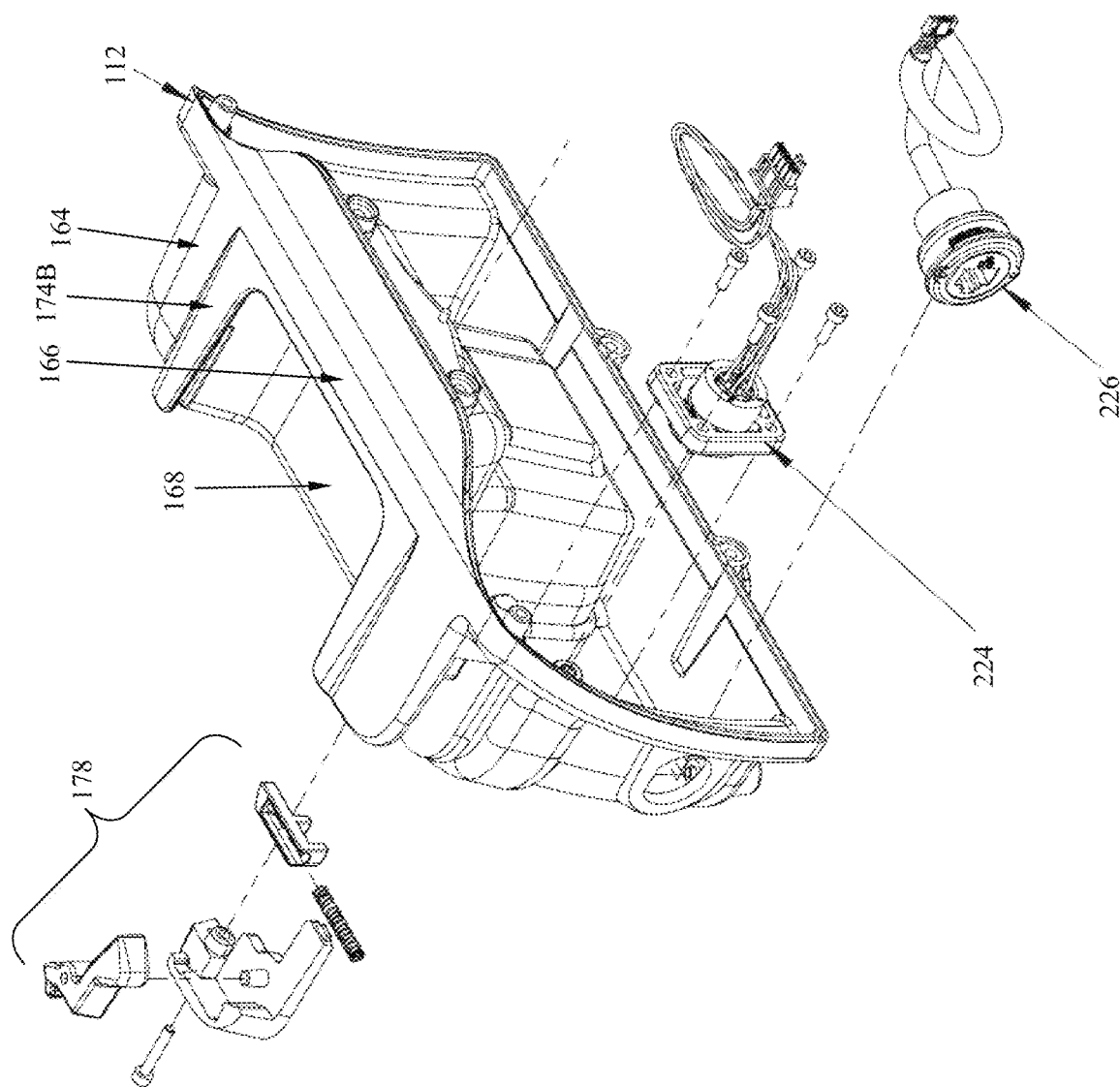
FIG. 6A is a front perspective, exploded view depicting a rear housing assembly in accordance with an embodiment of the disclosure.
Figure 6B:
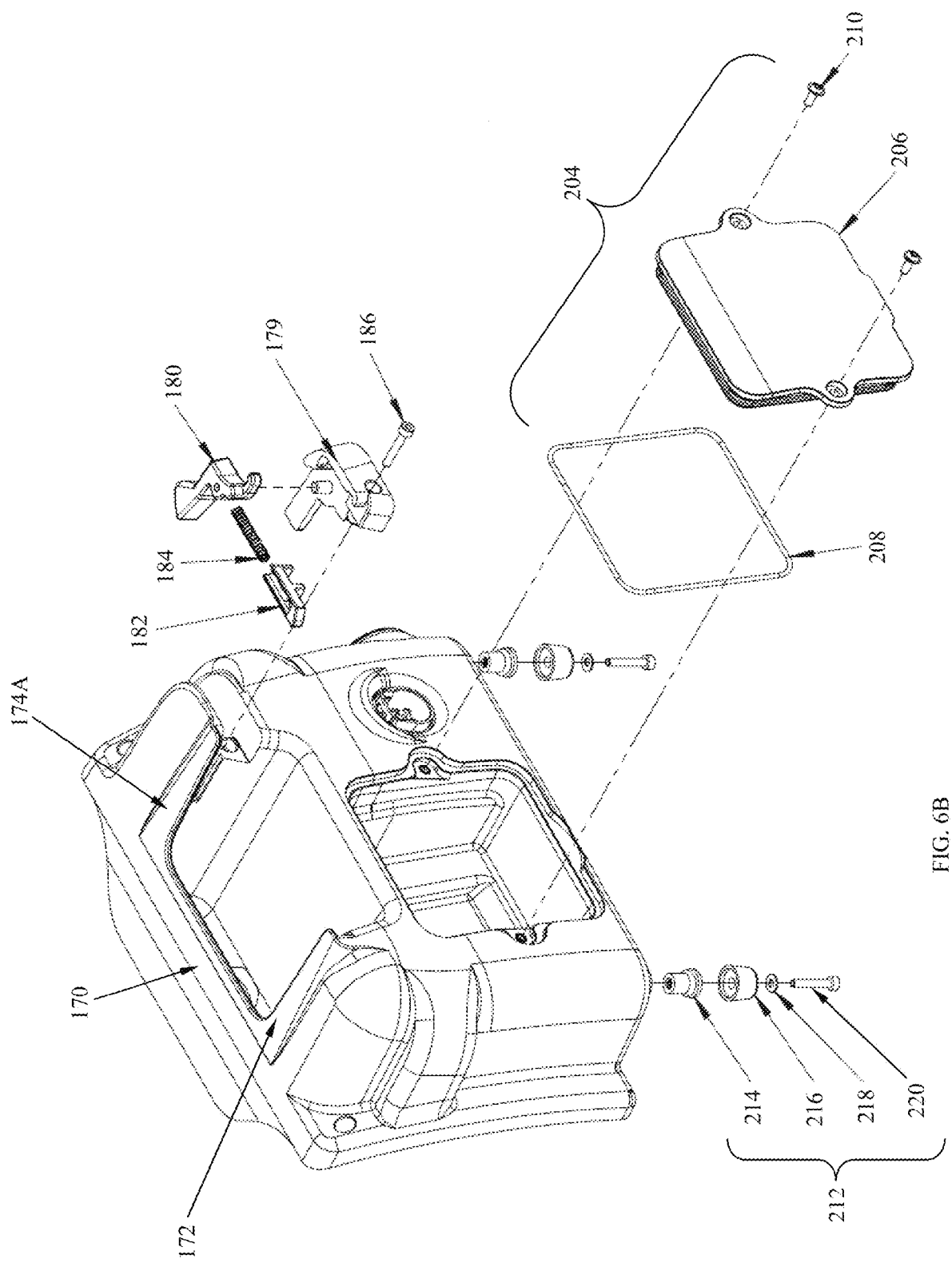
FIG. 6B is a rear perspective, exploded view depicting the rear housing assembly of FIG. 6A.

The housing 102 can generally form a protective shell surrounding internal components of the syringe pump 100. With additional reference to FIGS. 3-6B, the housing 102 can include a front housing assembly 110 and a rear housing assembly 112. FIG. 3 depicts an exploded view of a syringe pump 100 in which the front housing assembly 110 and the rear housing assembly 112 are separated from one another, in accordance with an embodiment of the disclosure. FIGS. 4A-B depict front and rear exploded, perspective views of the front housing assembly 110, in accordance with an embodiment of the disclosure. FIG. 5 depicts a close up view of an infusion line retention passage of the front housing assembly 110, in accordance with an embodiment of the disclosure. FIGS. 6A-B depict front and rear exploded, perspective views of the rear housing assembly 112, in accordance with an embodiment of the disclosure.

The front housing assembly 110 can provide support for the user interface 104, which in some embodiments can include a display screen 114 and a keypad 116. The display screen 114 can be any suitable Graphical User Interface (GUI) display for use in controlling the syringe pump 100. For example, in an embodiment, the display screen 114 can be a multicolor Liquid Crystal Display (LCD), dot matrix display, Organic Light-Emitting Diode (OLED) display, and/or any other device capable of visually delivering and/or accepting information. In some embodiments, the display screen 114 can be appropriately sized to enable display of drug and/or patient information, infusate delivery parameters. In an embodiment, the display screen 114 measures approximately 180 mm×73 mm; although other display screen sizes are also contemplated. In some embodiments, the display screen 114 can be configured to display instructional video, for example, to aid caregivers in proper maintenance and use of the syringe pump 100. In some embodiments, the display screen 114 includes touchscreen capabilities, thereby enabling certain commands and/or instructions to be received by the display screen 114.

The keypad 116 can be located adjacent to the display screen 114, and can present a variety of buttons and indicator lights. In some embodiments, push buttons requiring physical mechanical actuation can be utilized on the keypad 116 to enter certain user commands, including on/off power; audible alarm mute; and starting and stopping the delivery of infusate. Additional or fewer buttons on the keypad 116 are also contemplated. Physical mechanical actuation buttons, for primary or redundant purposes, provide increased safety and reliability to operators in cases where touchscreen capabilities of a display screen 114 are not properly functioning, or are otherwise difficult to correctly manipulate. Accordingly, the inclusion of a user interface 104 having both a display screen 114 and keypad 116 provides the flexibility of a screen interface, as well as the enhanced safety and reliability of physical control buttons. Additional information regarding user interface 104 can be found in WO 2019/055516A2, the disclosure of which is hereby incorporated by reference in its entirety.

The syringe receptacle 108 can be defined between a portion of the front housing assembly 110 and a syringe ledge 118. In an embodiment, the syringe ledge 118 can be operably coupled to the front housing assembly 110, for example, via one or more fasteners 120. The syringe receptacle 108 can be configured as an elongate cavity extending across the front of the syringe pump 100 configured to accept syringe barrels of a variety of shapes and sizes when loaded into the syringe pump 100. In an embodiment, the front housing assembly 110 and/or syringe ledge 118 can include a taper shaped and sized such that the syringe receptacle 108 is configured to accept syringes with syringe barrels that increase in diameter in proximity to the plunger.

The syringe receptacle 108 provides a cavity in the syringe pump 100 that remains open to the front of the syringe pump 100, such that a loaded syringe is readily and sustainably visible. In some embodiments, the syringe receptacle 108 is located below the display screen 114 of the user interface 104. Location of the syringe receptacle 108 below the user interface 104 can be advantageous, as any unintended fluid leakage from the syringe will naturally flow downwards due to gravity and away from the user interface 104, thereby avoiding potential damage to electronic and/or mechanical features of the user interface 104.

Accordingly, the syringe receptacle 108 can be somewhat spatially isolated from the remainder of the syringe pump 100 in the event of damage to the syringe or other leakage during loading, unloading, or manipulation. Additionally, because the display screen 114 is located above the syringe receptacle 108, the display screen 114 is generally not visually obstructed by the presence of a syringe loaded in the syringe receptacle 108. That is, the location of the display screen 114 above the syringe receptacle 108 enables unobscured visibility of both the syringe and display screen 114 during operation of the pump 100.

In some embodiments, the syringe receptacle 108 further includes an infusion line retention passage 122, also referred to as a tube guide, at an end of the syringe receptacle 108 opposite to the syringe drive assembly 106. The retention passage 122 provides a narrow passage or groove in which an infusion line in fluid communication with a syringe loaded into the syringe receptacle 108 can pass.

As depicted in FIG. 5, in an embodiment, the retention passage 122 can be defined by a channel 124 shaped and sized to accept a portion of infusion tubing. The channel 124 can be configured to bend the infusion tubing in at least two places, thereby forcing an axis of the infusion tubing proximal to the syringe to be offset from an axis of the infusion tubing exiting the front housing assembly 110. In an embodiment, the retention passage 122 can further include a hook structure 126 configured to retain the portion of infusion tubing within the channel 124. The hook structure 126 can be positioned above the portion of the infusion tubing exiting the front housing assembly 110, thereby securing the infusion tubing within the channel 124 and retaining the infusion tubing in a fixed position relative to the front housing assembly 110. Accordingly, the retention passage 122 can inhibit the infusion line from being unintentionally pulled away from the syringe pump 100 after loading, as such pulling of the infusion line will meet resistance from the retention passage 122, rather than any point where the infusion line is connected to a syringe located within the syringe receptacle 108.

As depicted in FIG. 4A, the syringe pump 100 can include a flange capture device 128 in proximity to the syringe receptacle 108, opposite to the retention passage 122. In an embodiment, the flange capture device 128 can include a shiftable retainer 130 configured to shift relative to the front housing assembly 110, for example, along an axis generally parallel to an axis of the syringe receptacle 108, thereby enabling the shiftable retainer 130 to capture the flange of a syringe barrel between the shiftable retainer 130 and a portion 131 of the housing 102. The flange capture device 128 can further include a biasing member 132 and clip assembly 134A/B configured to bias the shiftable retainer 130 towards the front housing assembly 110, as an aid in retention of the flange of a syringe barrel between the shiftable retainer 130 and the portion 131 of the housing 102. In some embodiments, the shiftable retainer 130 can be configured to maintain a fluid tight seal with the front housing assembly 110, for example via a sealing member 133, to inhibit fluid from entering the front housing assembly 110.

As depicted in FIG. 4B, a flange capture sensor 136 can be operably coupled to the flange capture device 128 on the inside of the front housing assembly 110. The flange capture sensor 136 can be configured to electronically sense when a syringe barrel flange is captured between the shiftable retainer 130 and the portion 131 of the housing 102, and therefore when a syringe is loaded into the syringe receptacle 108. In an embodiment, the flange capture sensor 136 can include an optical sensor 138 and a flag member 140. The flag member 140 can be operably coupled to the shiftable retainer 130, for example via the clip assembly 134A/B, such that when the shiftable retainer 130 is shifted outwardly, away from the front housing assembly 110, the flag member 140 shifts and/or pivots relative to the optical sensor 138, such that the optical sensor 138 registers the movement of the flag member 140 as an indication that the shiftable retainer 130 is at least partially extended or displaced, and that a syringe is loaded into the syringe receptacle 108.

As depicted in FIG. 4A, the syringe pump 100 can further include a barrel clamp device 142. In an embodiment, the barrel clamp device 142 can be located in proximity to the flange capture device 128, and/or generally underneath the keypad 116 on the front housing assembly 110. The barrel clamp device 142 can include a barrel clamp lever 144 configured to shift and rotate relative to the front housing assembly 110, for example, along an axis generally orthogonal to an axis of the syringe receptacle 108, thereby enabling the barrel clamp lever 144 to capture the barrel of a syringe between the barrel clamp lever 144 and a portion of the syringe ledge 118. The barrel clamp device 142 can further include a biasing member 146, rod 148, guide 150, housing 152 (see FIG. 4B), and fastener 154 configured to bias the barrel clamp device 142 away from the front housing assembly 110. In some embodiments, the barrel clamp lever 144 can be reversibly locked in a non-engagement position for ease in loading an unloading of a syringe into and out of the syringe receptacle 108.

As depicted in FIG. 4B, a barrel clamp sensor 156 can be operably coupled to the barrel clamp device 142 on the inside of the front housing assembly 110. The barrel clamp sensor 156 can be configured to electronically sense when a barrel of a syringe is captured between the barrel clamp lever 144 and a portion of the syringe ledge 118, and therefore when a syringe is loaded into the syringe receptacle 108. In an embodiment, the barrel clamp sensor 156 can include a linear potentiometer configured to sense the degree to which the barrel clamp lever 144 is extended or displaced from the front housing assembly, and therefore the approximate diameter of a syringe loaded into the syringe receptacle 108. In some embodiments, the sensed approximate diameter of the syringe can be used for syringe characterization.

The front housing assembly 110 can define one or more apertures 158 adjacent to which one or more audio speakers 160, voice synthesizer chips, piezoelectric buzzers, or the like can be mounted. In an embodiment, the speakers 160 can be equipped to provide a full range of audio output including commands, alerts, and informative communications. In some embodiments, the front housing assembly 110 further includes a remote dose cord receptacle 162, configured to receive input from a remote dose controller. In some embodiments, the remote dose cord receptacle 162 can include a USB port 163 or other appropriate input/output (I/O) interface port for connecting the syringe pump 100 to a network, computer or peripheral device having software configured to interface with the syringe pump 100.

As depicted in FIG. 6A-B, the rear housing assembly 112 generally includes a variety of contoured surfaces and shapes to protect the internal components of the syringe pump 100. The top portion 164 of the rear housing assembly 112 can provide features defining a handle 166. In some embodiments, the handle 166 can be integrally molded or formed into the outer surface of the rear housing assembly 112, and can be partially defined by a recess 168 in the top portion 164 of the housing 112. The handle 166 can provide a convenient structure for a person to grasp, manipulate, and move the syringe pump 100. The integrally formed nature of the handle 166, with the rest of the rear housing assembly 112, enables the syringe pump 100 to be more easily cleaned after use. By contrast, a non-integral handle and housing arrangement having a separate hinge or attachment features, can present a much more difficult component or assembly to clean.

In some embodiments, the handle 166 can be part of a retaining feature 170, configured to provide releasable locking engagement with other infusion pumps, a pump rack, or related medical components. The retaining feature 170 can include an upper lip portion 172 that extends inwardly around the recess 168 located at the top portion 164 of the rear housing assembly 112. In some embodiments, the upper lip portion 172 can extend around three sides of the recess 168 to form a general "U" shape when viewed from above. In some embodiments, a section of the upper lip portion 172 in the middle of the retaining feature 170 can comprise the handle 166. A recessed space in which a person can place his or her fingers in order to readily grasp the handle 166, can be positioned beneath the handle 166 portion of the upper lip portion 172.

The retaining feature 170 can further include one or more receiving grooves 174, which can be positioned underneath the upper lip portion 172. In some embodiments, the retaining feature 170 includes a pair of receiving grooves 174A-B positioned on opposite sides of the retaining feature 170. In an embodiment, the receiving grooves 174 can be configured as slots that progressively narrow in structure and converge inwardly from a rear face 176 of the rear housing assembly 112. In some embodiments, the receiving grooves 174 can be configured to receive a portion of a bottom extending projection 188 of another infusion pump, when a plurality of infusion pumps are operably coupled together in a stacked configuration.

In some embodiments, the retaining feature 170 can include a latch assembly 178, configured to selectively lock the infusion pump 100 to other infusion pumps, a pump rack, or related medical components. The latch assembly 178 can be positioned on one side of the retaining feature 170 proximal to one of the receiving grooves 174A. The latch assembly can include a latch body 179, button 180, catch 182, biasing member 184, and fastener 186. In an embodiment, the catch 182 can be manipulated by the button 180 between an engaged position and a disengaged position. The biasing member 184 can bias the catch 182 to the engaged position. In an embodiment, the catch 182 can be configured to produce an audible noise, such as a "click" sound, to provide auditory confirmation of engagement with a corresponding member of another infusion pump, pump rack, or the like, loaded into the receiving grooves 174.

Figure 7:
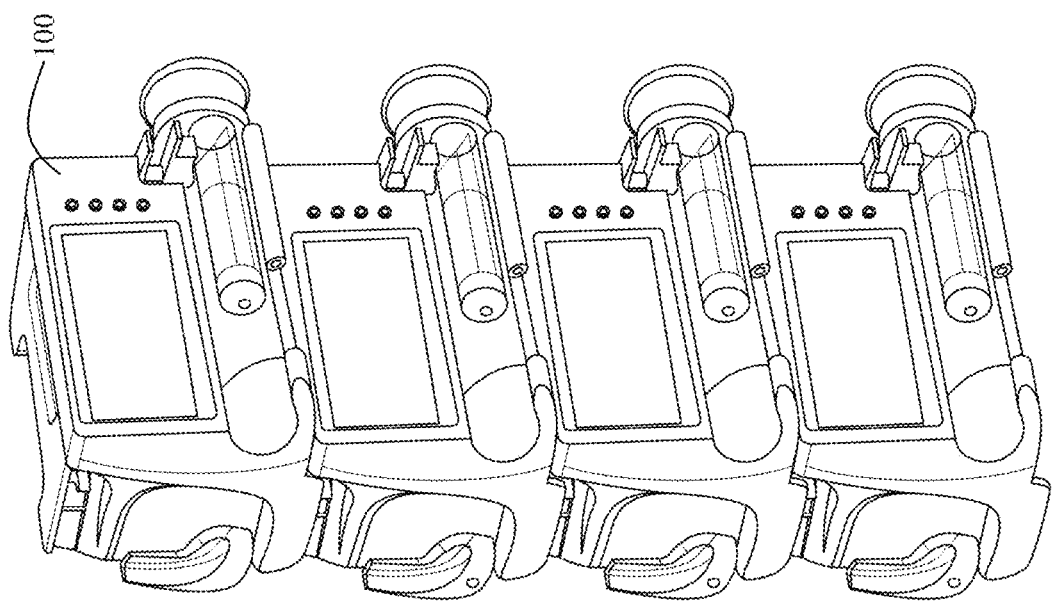
FIG. 7 is a perspective view depicting a stacked arrangement of infusion pumps in accordance with an embodiment of the disclosure.

As depicted in FIG. 2, the rear housing assembly 112 can include a downwardly extending projection 188 on a bottom portion 190 of the syringe pump 100. In an embodiment, the extending projection 188 can be shaped and sized to be received within corresponding grooves (similar to receiving grooves 174) of other pumps or medical devices, thereby enabling the syringe pump 100 to be readily stacked with other medical devices having such a corresponding retaining feature. The extending projection 188 can include a forward portion 192 and one or more rearward portions 194. In some embodiments, the forward portion 192 can generally form a "U" shape. The rear portions 194A-B can each provide segments of wider separation than the sides of the forward portion 192. In an embodiment, rearward portions 194A-B can include a flange 196 configured to provide a feature for sliding engagement with the receiving grooves 174. Accordingly, the downwardly extending projection 188 can provide a structure that can be releasably slid into and engaged within the receiving grooves of the retaining feature of a corresponding device. This type of coupling effectively provides so-called "tongue and groove" type retention. Accordingly, the generally "U" shaped retaining feature 170 and extending projection 188 can enable multiple infusion pumps 100 to be stacked on one another in an engaged tongue and groove arrangement. For example, referring to FIG. 7, a stack of infusion pumps 100, in which the downward extending projection 188 of each pump is received within a corresponding retaining feature 170 of the infusion pump 100 on which it is stacked, is depicted in accordance with an embodiment of the disclosure.

Figure 8:
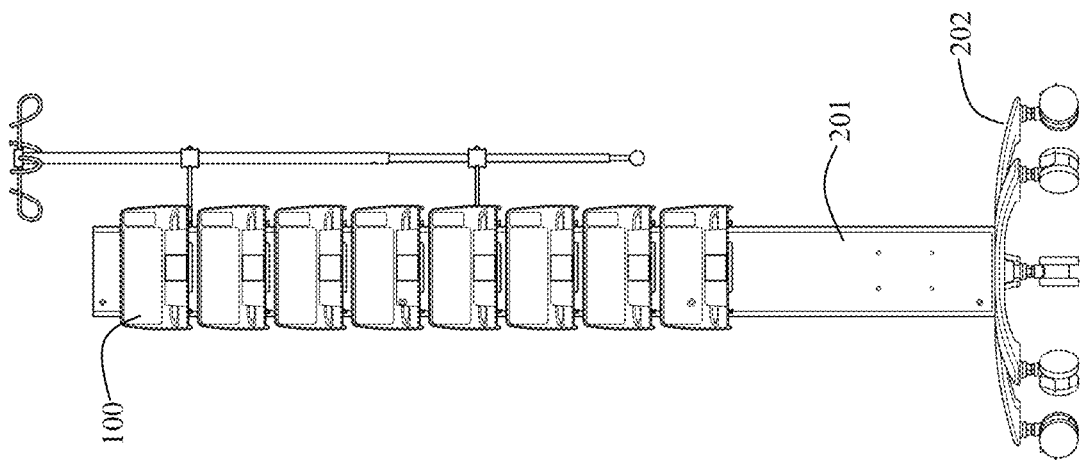
FIG. 8 is a perspective view depicting a racked arrangement of infusion pumps in accordance with an embodiment of the disclosure.

In other embodiments, a plurality of infusion pumps 100 can be positioned relative to one another on a rack 201. Referring to FIG. 8, a racked arrangement of infusion pumps 100 is depicted in accordance with embodiments of the disclosure. In an embodiment, the rack 201 can include the equivalent of, for example, eight extending projections configured to be received within the retaining features of up to, for example, eight infusion pumps 100. The rack 201 can optionally include a wide wheelbase with legs 202 to inhibit the rack from tipping. In some embodiments, the rack 201 can be provided with an AC power supply and/or a consolidated ethernet connection. Accordingly, the rack 201 enables the individual installation and removal of infusion pumps 100, thereby enabling customized patient-specific infusion pump configurations.

Figure 9:
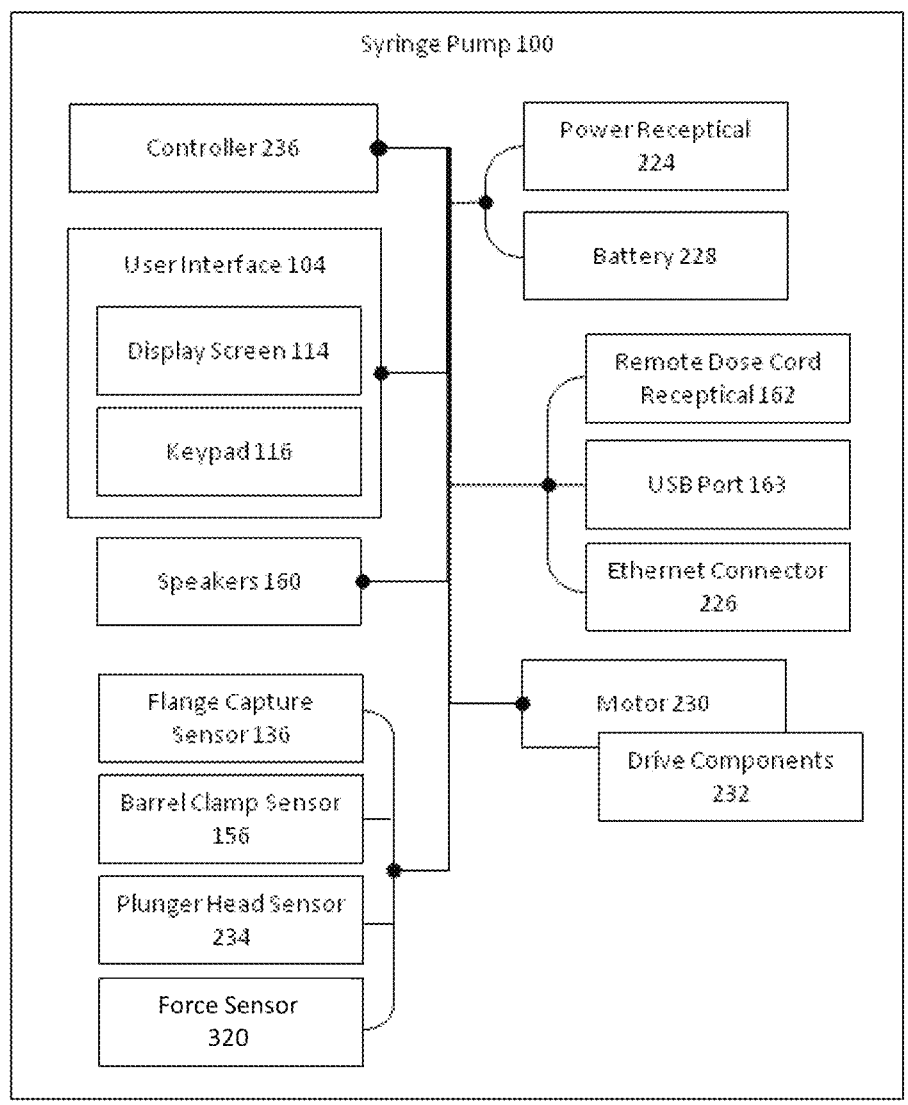
FIG. 9 depicts a general system diagram of a syringe pump in accordance with an embodiment of the disclosure.

As depicted in FIG. 6B, the rear housing assembly 112 can also include a battery door cover assembly 204. The battery door cover assembly 204 can include a plate 206 and a sealing gasket 208, which can be selectively coupled to the rear housing assembly 112 by one or more fasteners 210. The battery door cover assembly 204 can selectively provide access to a battery of the syringe pump, and can be generally rectangular in shape, but can include curved perimeter features to accommodate the fasteners 210. Accordingly, a battery 228 (as depicted in FIG. 9) can be readily accessed, removed and replaced in rear housing assembly 112.

Additionally, the rear housing assembly can include one or more feet 212. For example, in an embodiment, the syringe pump can include two feet. Each mounting foot 212 can include a well nut 214, a mounting pad 216, a washer 218, and a fastener 220. In other embodiments, the feet 212 can be integrally molded into the housing 102 and can include less or other components. In some embodiments, a portion of the feet 212 (e.g., the mounting pad 216) can be constructed of a resilient material having a desired coefficient of friction, such as rubber, to improve surface contact and inhibit sliding. The feet 212 can be positioned on the syringe pump 100 so as to avoid interference with stacking and/or mounting. For example, in an embodiment the feet 212 can serve to raise the backside of the housing 102, so as to provide clearance for the downwardly extending projection 188.

As depicted in FIG. 6A, other features on the rear housing assembly 112 include a power receptacle 224 and an ethernet connector 226. The power receptacle 224 can interface directly with a power cord, or alternatively, with a power connector contained on a pump rack 201. In the case of connection to a power cord, the power receptacle 224 can provide a mechanical lock and retaining feature that inhibits the power cord from being unintentionally pulled from operative engagement with the syringe pump 100, thereby inhibiting a sudden and unintended loss of power. The power receptacle 224 can also be configured with a tapered bevel structure configured to serve as an aid in improving interconnection with a corresponding power connector on a rack, as visibility can be limited during the process of connecting the syringe pump 100 to the rack.

In some embodiments, male and female connector portions of the power receptacle 224 can be keyed or otherwise restricted or controlled in orientation such that interlocking of the male and female components can only be made in a specific orientation. This can be advantageous in assisting proper alignment of pins, e.g., (+) to (+), and (−) to (−). The power receptacle 224 connector portions can be keyed such that they cannot be connected in an improper orientation. In some embodiments, the power cord can be a "right angle" connector, so as to minimize the profile of the syringe pump 100 and decrease possible entanglements with other cords and/or connectors.

The location of the ethernet connection 226 can be configured to provide a convenient access for connection to other pumps, racks or communication devices that utilize ethernet connections for data transfer. The ethernet connector 226 can be "ingress-protection" (or "IPX") rated and does not require a cover. In some embodiments, the ethernet connection 226 can be utilized to enable multiple pumps 100 within a rack or stack to communicate with a network and/or directly with other pumps 100 in the rack or stack. For example, two or more pumps can work in unison to deliver a required dose of medicament, wherein a first pump communicates delivery parameters, such as the amount of medicament delivered, to a second pump.

Additional information pertaining to the housing assemblies, handle, retaining feature and related features can be found in WO 2019/018658A2, the disclosure of which is hereby incorporated by reference in its entirety.

Referring to FIG. 9, a general system diagram of a syringe pump 100 is depicted in accordance with an embodiment of the disclosure. As previously described the syringe pump 100 can include a user interface 104 (which can include a display screen 114 and keypad 116), a battery 228, power receptacle 224, Ethernet connection 226, remote dose cord receptacle 162, USB port 163, and one or more speakers 160. In some embodiments, the syringe pump 100 can further include a motor 230 and drive components 232 to drive the syringe drive assembly 106. A controller 236 can be configured to control operation of the motor 230 and drive components 232.

The controller 236, which can be powered by the battery 228 and/or power receptacle 224, can include one or more processors and/or a memory. In some embodiments, the controller 236 is in electrical communication with the user interface 104, the remote dose cord receptacle 162, the USB port 163, and the Ethernet connection 226, for the purpose of receiving information from and/or transmitting information to users of the syringe pump 100.

The controller 236 can additionally be in electrical communication with the flange capture sensor 136, barrel clamp sensor 156, and plunger head sensor 234, and can be configured to receive data sensed by the sensors 136, 156, 234 for further processing. In some embodiments, the processor is configured to detect: whether a syringe is loaded into the syringe receptacle 108, the size of the syringe, how much medicament has been deliver and/or remains in the syringe, and the presence of an occlusion. An example method of syringe characterization that can be employed is embodied in U.S. Patent Publ. No. 2015/0297832, entitled "Syringe Characterization," the contents of which are hereby incorporated by reference herein. An example method of occlusion detection that can be employed is embodied in U.S. Patent Publ. No. 2015/0133890, entitled "Occlusion Detection," the contents of which are hereby incorporated by reference herein.

Some embodiments of the syringe pump 100 can make use of a Field Replaceable Unit (FRU) design, which enables the various components of the syringe pump 100 to be readily upgraded and/or replaced. FRU components provide ease of pump manufacture as well as simplified maintenance and replacement. In general, FRUs can be categorized into three groups: wear components (e.g., components in need of replacement due to normal wear and tear, breakage, end-of-life, etc.); improvements in technology (e.g., upgrades to communications, Wi-Fi, Bluetooth, USB, display, etc.) and functionality upgrades (e.g., syringe security, patient-controlled analgesia or "PCA", target-controlled infusion or "TCI", etc.). In some embodiments, FRUs can include components or groups of components of the syringe pump 100. Examples of such FRUs can include: the front housing assembly 110, the rear housing assembly 112; a display screen 114; a battery pack 228 with a power gauge; a power supply 224; various circuitry and/or wireless components; and the syringe drive assembly 106 or components thereof.

Figure 10A:
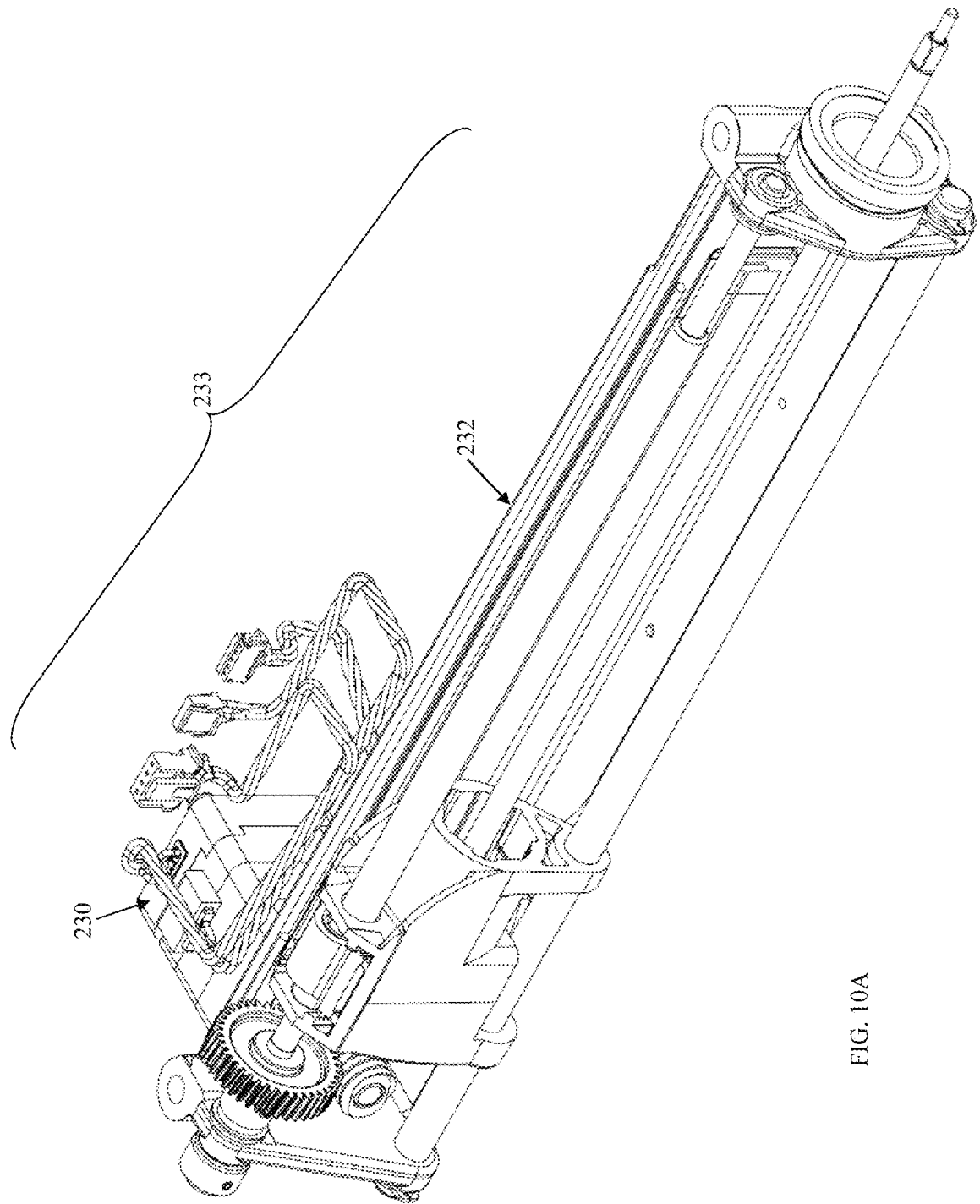
FIG. 10A is a perspective view depicting a motor and syringe drive components, in accordance with an embodiment of the disclosure.
Figure 10B:
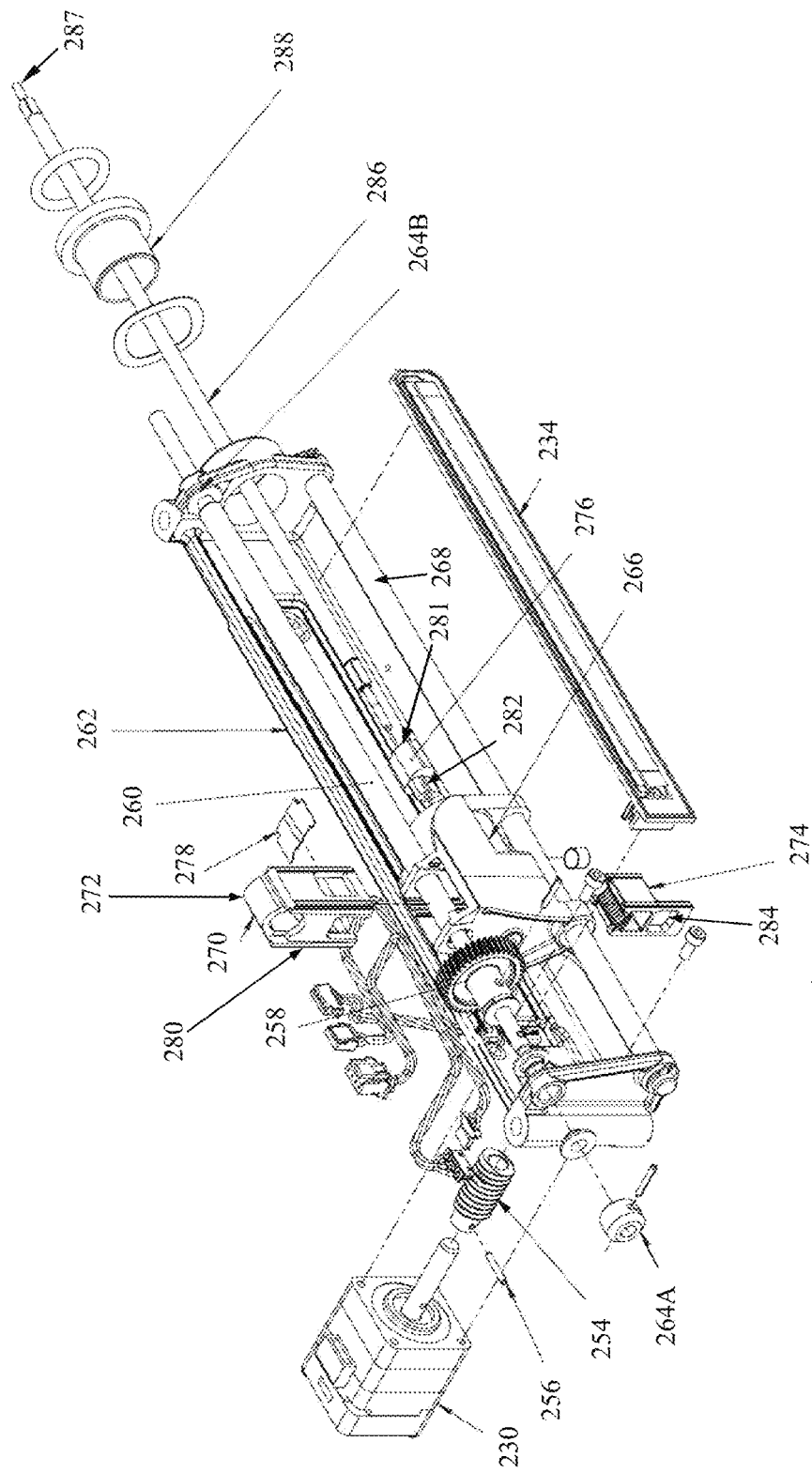
FIG. 10B is an exploded, perspective view depicting the motor and syringe drive components of FIG. 10A.

In an embodiment, the syringe drive assembly 106 generally includes a powertrain 233 and a plunger head assembly 290. Powertrain 233 can include a motor 230, syringe drive components 234, and plunger driver assembly 290 (as illustrated in. e.g., FIG. 12A). Referring to FIG. 10A, a perspective view of a motor 230 and syringe drive components 232 are depicted in accordance with an embodiment of the disclosure. In some embodiments, the motor 230 and syringe drive components 232 (collectively the powertrain 233) can be constructed as an aforementioned FRU. Referring to FIG. 10B, an exploded, perspective view of the motor 230 and syringe drive components 234 of FIG. 10A is depicted.

In an embodiment, the motor 230 can be a stepper motor and encoder configured to rotate in discrete step increments when electrical command pulses are applied. The motor 230 can be operably coupled to a worm gear 254, for example, via pin 256. Worm gear 254 can interface with a gear 258, which can be operably coupled to a lead screw 260. Lead screw 260 can be operably coupled to a drive train chassis 262, for example, via one or more hubs and/or bushings 264.

Although not explicitly illustrated in the drawings, it is to be appreciated and understood that one or more rubber or other suitable elastic components can be included in an embodiment of pump 100 to bias the one or more hubs and/or bushings 264 to a so-called "dead stop" against, for example, adjacent portions of drive components 232. An advantage of such a construction is that tolerances of drive components 232 and their assemblies do not need to be so relatively tight or precise to reduce mechanical slack or "slop" among the components and assemblies. Such reduction of mechanical slack or slop can advantageously reduce the time required, upon starting the pump, to reach a generally steady-state or generally electro-mechanically stable condition for acceptable pump performance.

A carriage assembly 266 can be operably coupled to the lead screw 260 and the drive train chassis 262, such that rotation of the lead screw 260 forces the carriage assembly 266 to shift or translate relative to the drive train chassis 262, thereby causing translation of plunger driver assembly 290. For example, in an embodiment, the carriage assembly 266 can be operably coupled to the drive train chassis 262 via a guide rod 268. A plunger head sensor 234 can be configured to determine positional data of the carriage assembly 266 relative to the drive train chassis. In an embodiment, the plunger head sensor 234 can be a linear potentiometer configured to sense the linear distance to which the carriage assembly 266 as shifted or translated along the guide rod 268.

Figure 11B:
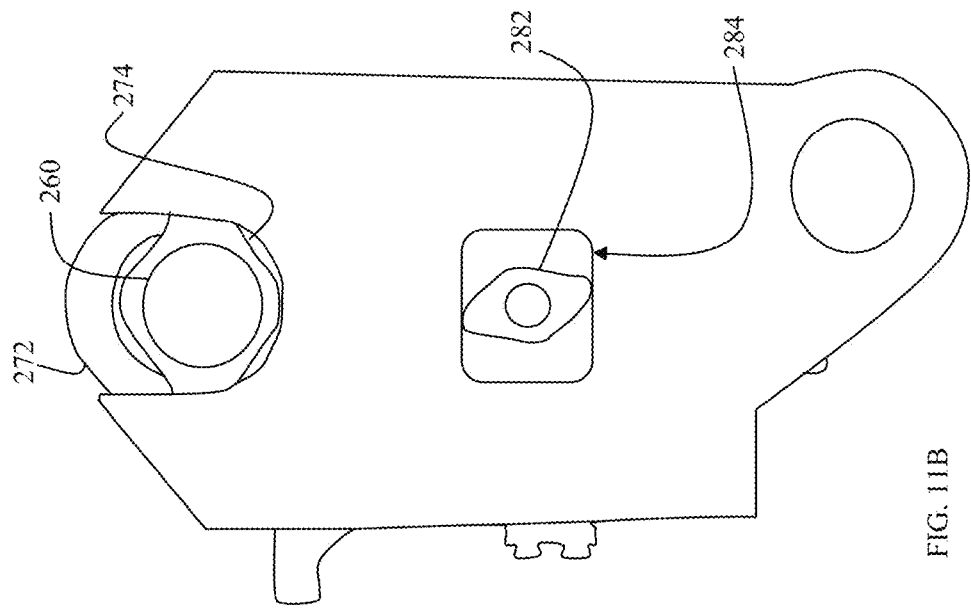
FIG. 11B is a plan view depicting the clutch assembly of FIG. 11A in a lead screw release position, in accordance with an embodiment of the disclosure.
Figure 11A:
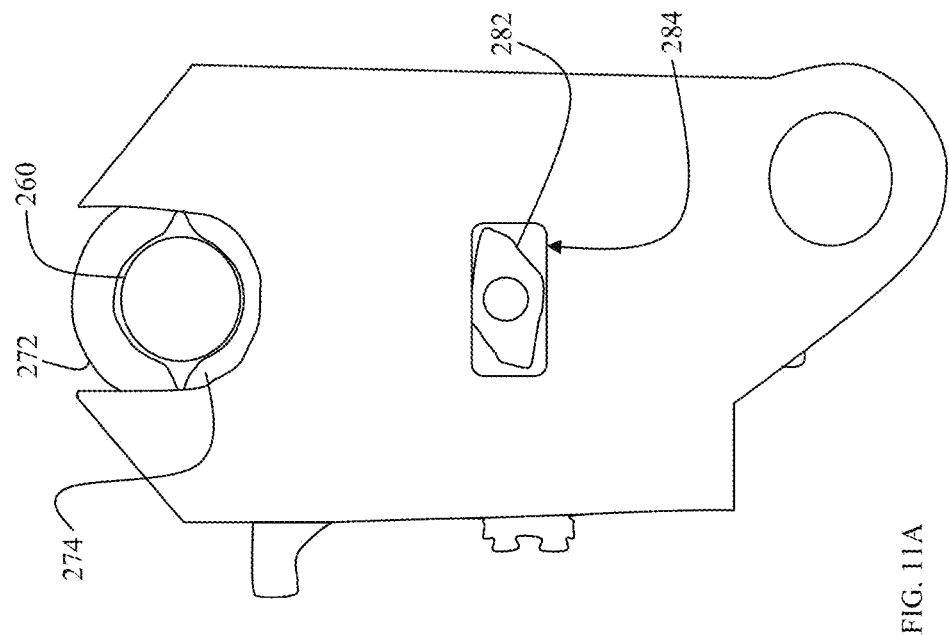
FIG. 11A is a plan view depicting a clutch assembly in a lead screw grip position, in accordance with an embodiment of the disclosure.
Figure 11D:
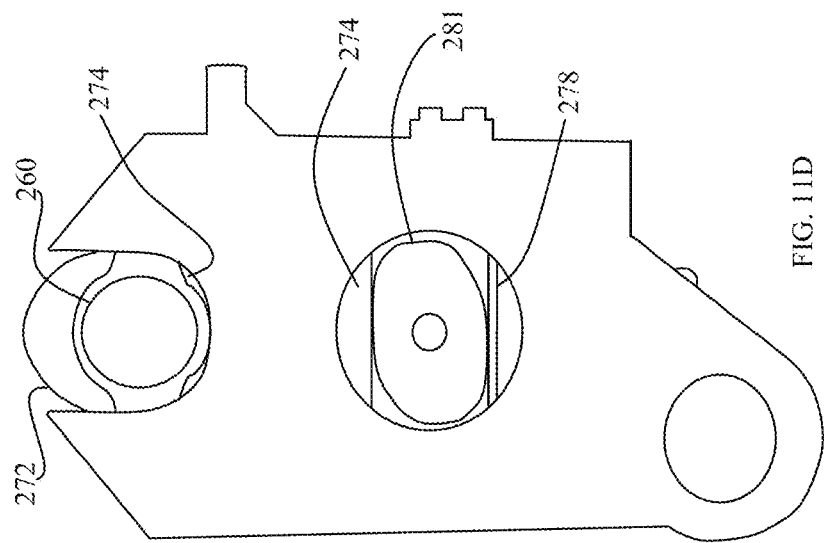
FIG. 11D is a plan view from the opposite perspective of FIG. 11B.
Figure 11C:
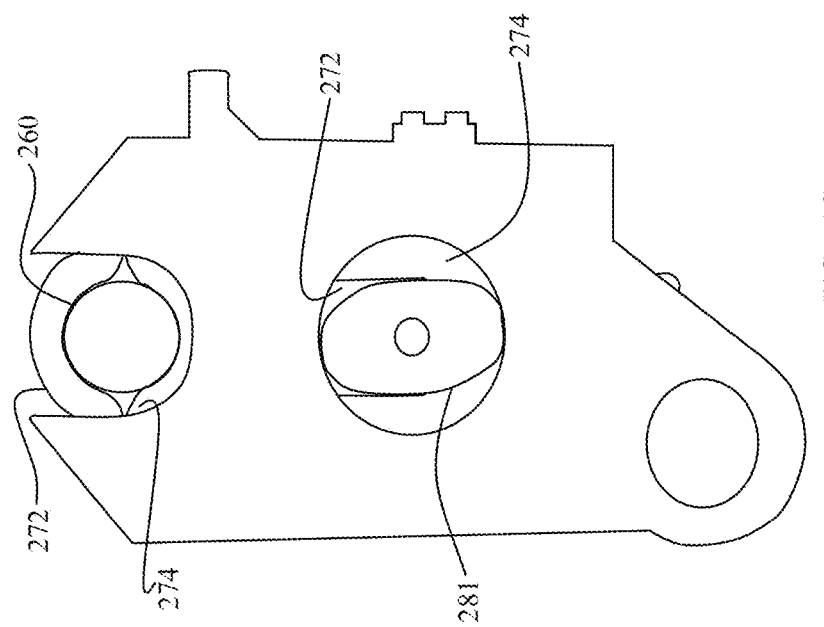
FIG. 11C is a plan view from the opposite perspective of FIG. 11A.
Figure 11E:
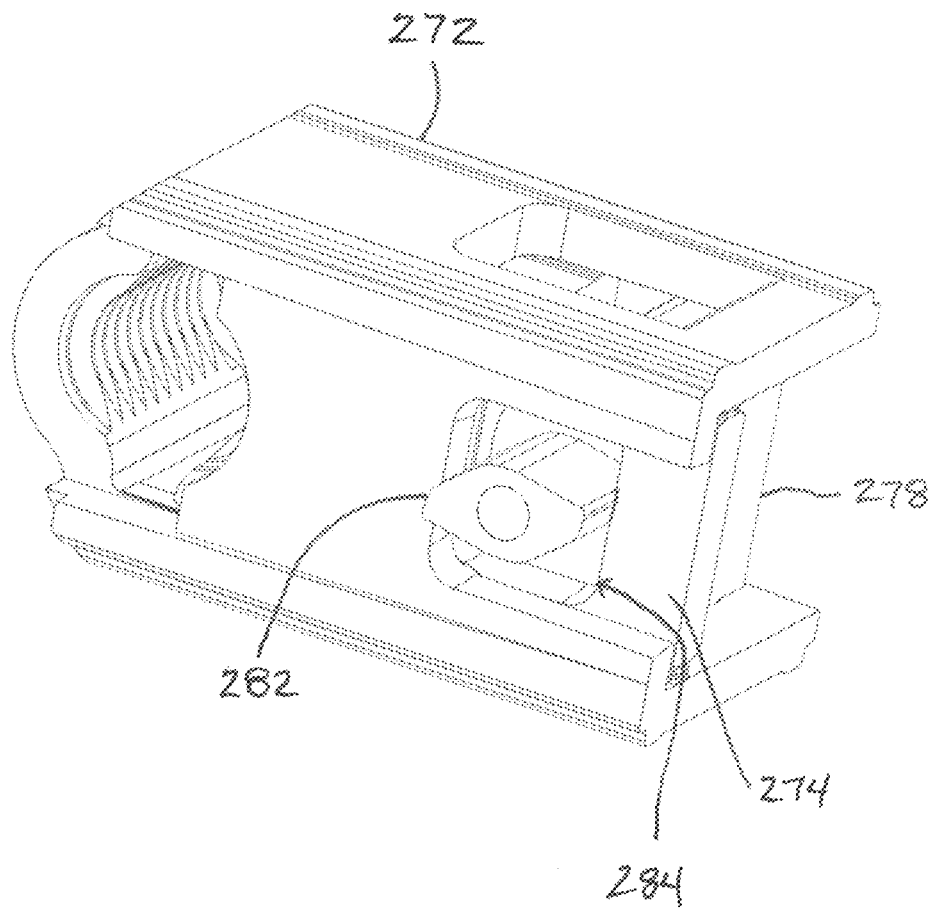
FIG. 11E is a perspective view of some of the clutch assembly components in a lead screw release position.
Figure 11F:
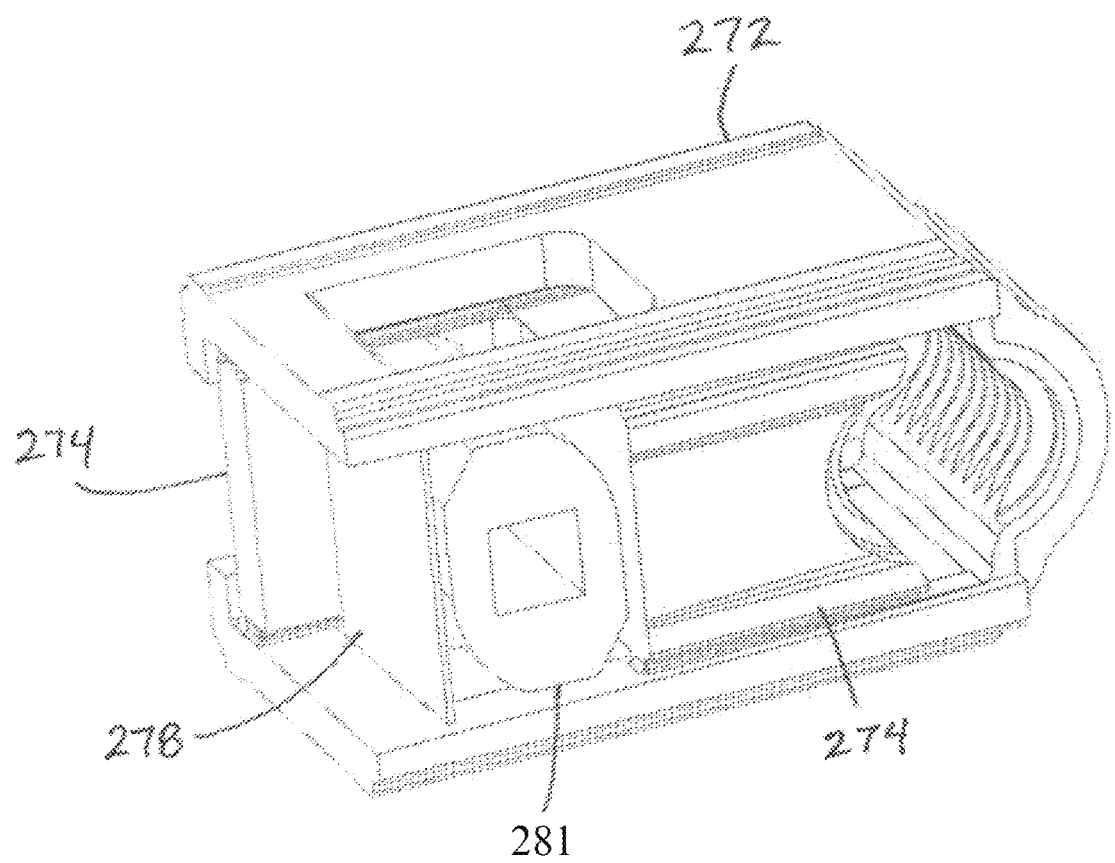
FIG. 11F is a perspective view from the opposite perspective of FIG. 11E.

In an embodiment, the carriage assembly 266 can be selectively coupled to the lead screw 260 by a clutch assembly 270. Referring now to FIGS. 11A-11F, the clutch assembly 270 can include a half nut frame 272, inner half nut 274, cam 276, and spring 278. The half nut frame 272 can define a housing 280 configured to at least partially receive the cam 276 and inner half nut 274 therein. The spring 278 can couple to a bottom portion of the housing 280 to aid in retaining the cam 276 and the inner half nut 274 within the housing 280. Cam 276 includes a first lobe 281 and a second lobe 282. In an embodiment, first lobe 281 has greater lift than second lobe 282. In embodiments, first lobe 281 is operable in a space defined between inner half nut 274 and spring 278, while inner half nut 274 includes a cutout 284 and second lobe 282 of the cam 276 is operable within cutout 284. Generally, rotation of cam 276 causes the inner half nut 274 to shift relative to the half nut frame 272 between a lead screw grip position (as depicted in FIGS. 11A and 11C) and lead screw release position (as depicted in FIGS. 11B and 11D). In an embodiment, first lobe 281 is operable to move the half-nuts into engagement with lead screw 260 and second lobe 282 is operable to move the half-nuts into disengagement with lead screw 260.

It is to be appreciated and understood that, in an embodiment, the half nut frame 272 and the inner half nut 274 are capable of translational movement relative to each other. Accordingly, half nut frame 272 and inner half nut 274 cooperate mechanically, to enable carriage assembly 266 to engage and/or disengage the lead screw 260; and the carriage assembly 266 can act to acceptably confine the translational movements of the half nut frame 272 and the inner half nut 274.

In an embodiment, the lead screw grip position can be the default position for the clutch assembly 270, such that the clutch assembly 270 is naturally biased towards gripping the lead screw. The greater size of first lobe 281 compared to second lobe 282 contributes to maintaining the clutch assembly in the default position engaged with the lead screw, as does biasing element 312 described below. In an embodiment, leaf spring 278 can be configured such that when clutch assembly 270 is in the lead screw grip position, spring 278 is biased against first lobe 281 to maintain the lead screw grip position. In an embodiment, cam 276 is not in contact with spring 278 in the lead screw release position. Additionally, cam 276 may be configured such that first lobe 281 is over-center in the lead screw grip position, further contributing to maintaining clutch assembly 270 in the lead screw grip position.

Accordingly, if an accidental external force is applied to the syringe pump 100, for example if the syringe pump 100 is accidentally bumped and/or falls, the arrangements described and depicted herein biasing clutch assembly 270 to the lead screw grip position can serve as an aid in inhibiting unwanted movement of the plunger driver assembly 290, and thereby inhibit unintended delivery of medicament from a syringe in pump 100.

The cam 276 can be operably coupled to a cam rod 286. In an embodiment, at least a portion of the cam rod 286 can have a substantially square cross section. The cam rod 286 can be operably coupled at one end to the cam 276, and can be operably coupled at the other end 287 to a plunger head assembly 290. The cam rod 286 can be supported by the carriage assembly 266, for example, via a bushing 288.

Figure 12A:
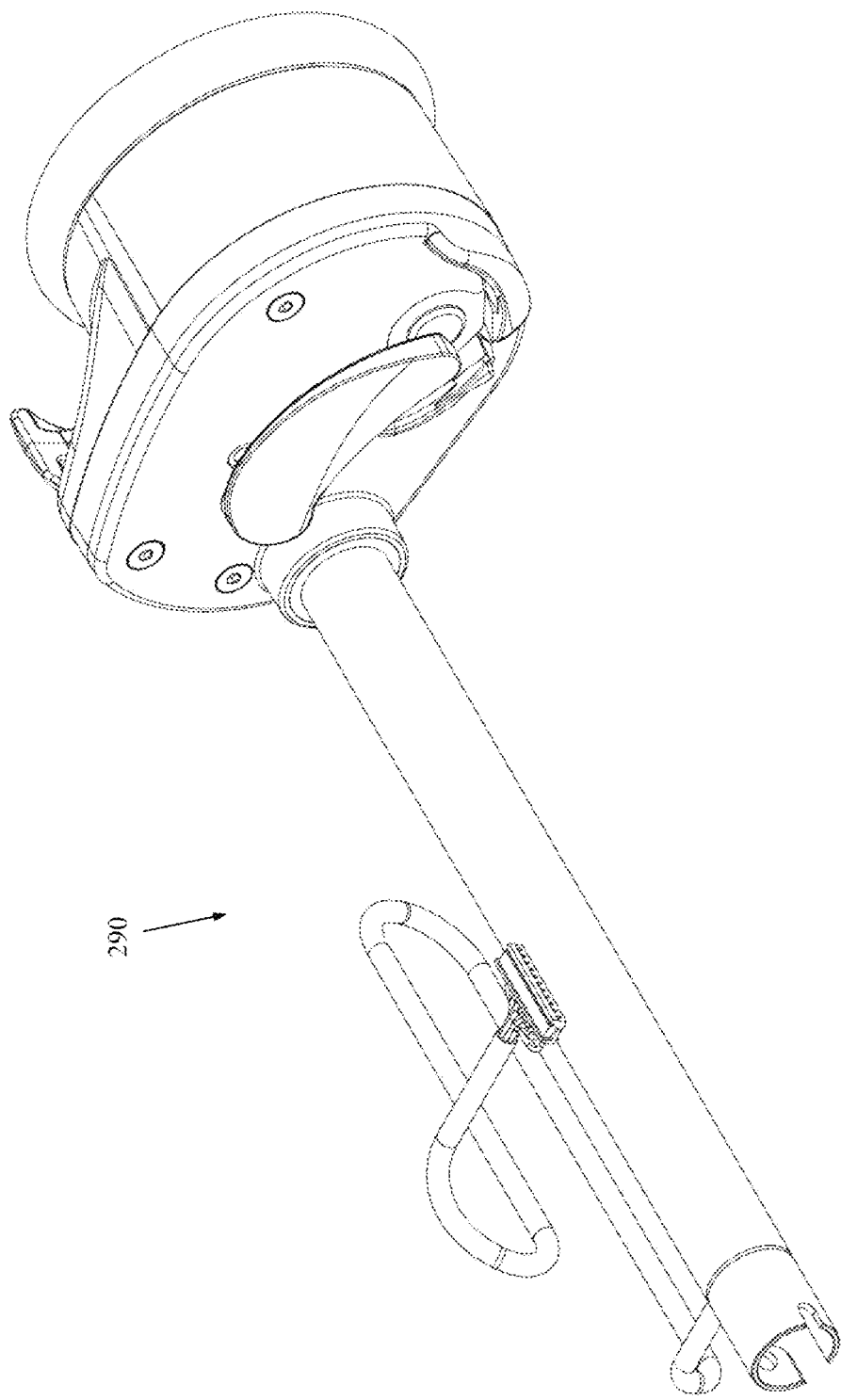
FIG. 12A is a perspective view depicting a plunger driver head assembly, in accordance with an embodiment of the disclosure.
Figure 12B:
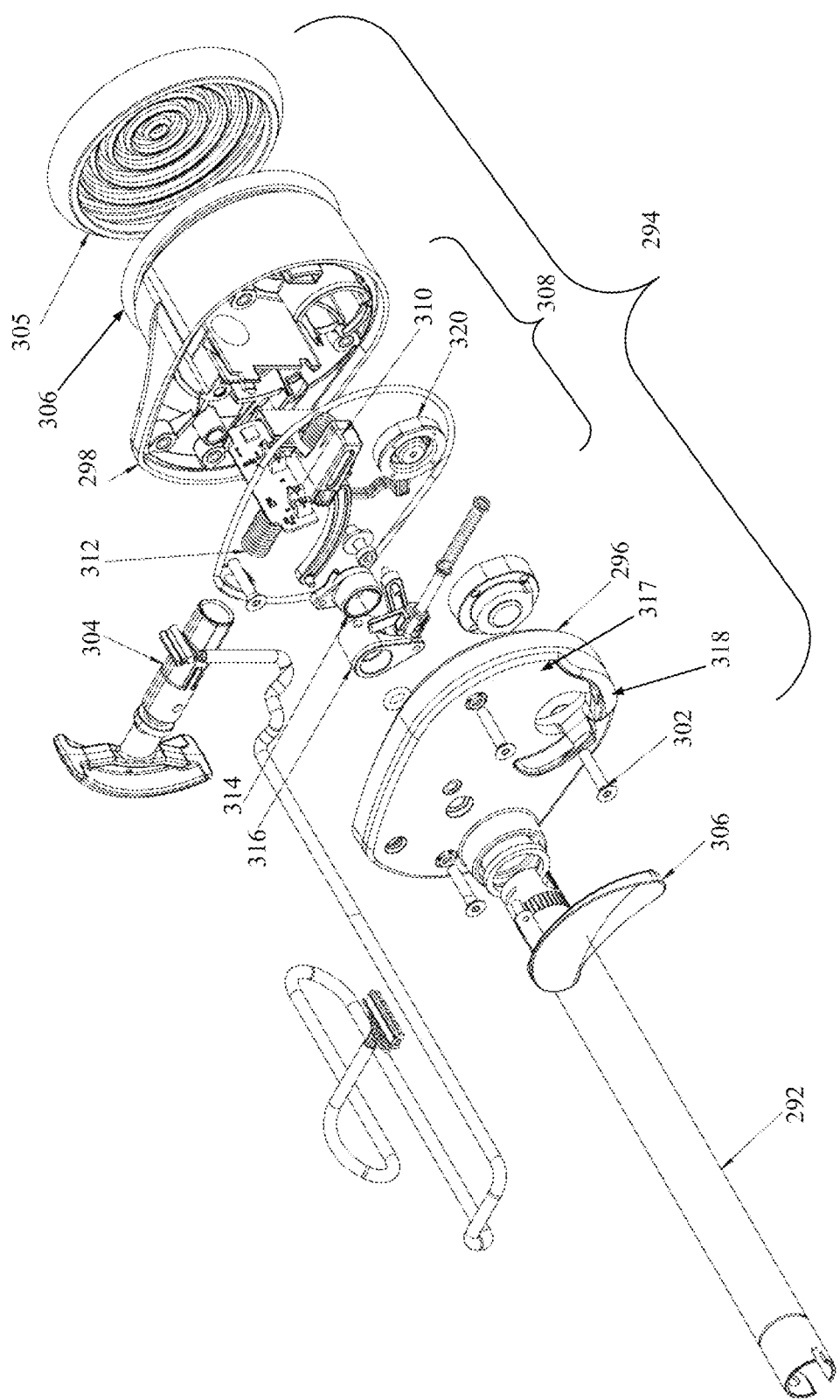
FIG. 12B is an exploded, perspective view depicting the plunger driver head assembly of FIG. 12A.

Referring to FIGS. 12A, a perspective view of plunger head assembly 290 is depicted in accordance with an embodiment of the disclosure. Referring to FIG. 12B, an exploded, perspective view of the plunger head assembly 290 of FIG. 12A is depicted in accordance with an embodiment of the disclosure. The plunger head assembly 290 can include a plunger tube 292 operably coupled to a plunger driver head assembly 294. In an embodiment, the plunger tube 292 is coupled at one end to the carriage 266 and coupled at the other end to the plunger driver head assembly 294. By way of attachment to carriage 266, plunger tube 292 of plunger head assembly 290 is thereby operably connected with lead screw 260 by way of clutch assembly 270. In an embodiment, the plunger tube 292 at least partially surrounds the cam rod 286, such that the cam rod 286 is at least partially housed within the plunger tube 292. The end 287 of the cam rod 286 opposite to the cam 276 can be operably coupled to the plunger driver head assembly 294.

The plunger driver head assembly 294 can include a front housing 296 and a back housing 298. The front housing 296 can be coupled to the back housing 298, for example, via one or more fasteners 302. A bumper 305 can be operably coupled to an outer face 307 of the back housing 298. In an embodiment, the bumper 305 can be generally rounded in shape and fabricated of a resilient material to absorb external forces acting upon the plunger driver head assembly 294. For example, in an embodiment, the bumper 305 can be configured to inhibit damage to the plunger head assembly should the syringe pump be dropped or knocked over. In an embodiment, the resilient bumper 305 can be configured to temporarily deform in order to absorb shock and/or external forces of a limited magnitude applied to the plunger driver head assembly 294 to inhibit damage to the syringe pump 100 and/or unintentional movement of the plunger driver head assembly 294 and corresponding unintended delivery of medicament from a syringe in pump 100 as a result of the external force or shock. In an embodiment, the resilient bumper 305 is capable of absorbing a sustained force of up to five Newtons.

In an embodiment, the bumper 305 and plunger driver head assembly 294 can be ergonomically molded to conform to the inner aspect of a user's hand to aid in one-handed manipulation of the plunger driver assembly 290 during loading and unloading of a syringe. A trigger 304 operably coupled to a flipper 306 and the clutch assembly 270 can extend from the plunger driver head assembly 294. In an embodiment, the trigger 304 can be positioned on the ergonomically molded plunger driver head assembly 294 where a user would normally position their fingers during loading and unloading of a syringe. The flipper, or plunger holder, 306 can be positioned on an inner face 317 of the front housing 296 and can include a generally curved arm that extends over a distal thumb press portion of a plunger of a syringe so as to removably secure the syringe to the plunger driver 182. In an embodiment, the interface 317 can include one or more supporting lips 318 configured to conform to a portion of a plunger of a variety of different shaped and sized syringes loaded into the syringe pump 100. The flipper 306 can be configured to rotate relative to the plunger driver head assembly 294 between a syringe plunger loading and unloading position and a syringe plunger capture position.

The trigger 304 can be operably coupled to an actuator assembly 308, which can include an actuator 310, biasing element 312, clutch release 314, and flipper actuator 316. In an embodiment, the biasing element 312 can be configured to bias the clutch release 314 in order to position the clutch assembly 270 to the lead screw grip position as aforedescribed, and bias the flipper actuator 316 to position the flipper 306 to a syringe plunger capture position. Conversely, depressing the trigger 304 can simultaneously shift the clutch release to position the clutch assembly 270 to the lead screw release position, and shift the flipper actuator 316 to position the flipper to a syringe plunger loading and unloading position. Accordingly, the trigger 304 can be spring-loaded, and can be configured to unlock the plunger driver assembly 290 from a locked state, such that the plunger driver assembly 290 can then relatively freely slide laterally when the trigger 304 is depressed.

A thumb press force sensor 320 can be positioned within the plunger driver head assembly 294 in proximity to the flipper 306, such that force sensor 320 can sense a force magnitude acting upon a syringe loaded into the syringe pump. In an embodiment, the force sensor 320 can sense a force applied by the plunger driver assembly 290 upon a syringe during operation. In some embodiments, the force sensor 320, (optionally in combination with, for example, one or more of the other sensors 136, 156, 234), can be utilized to detect the presence of an occlusion and/or characterize the syringe.

Figure 13A:
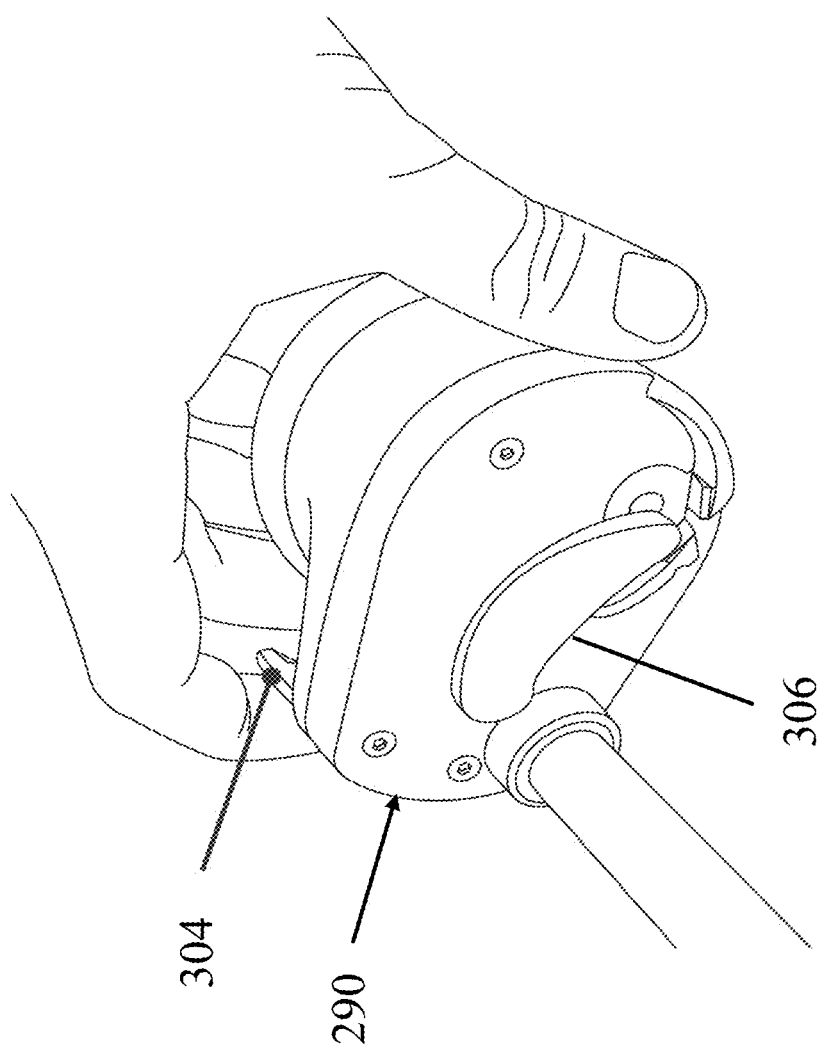
FIG. 13A is a perspective view depicting a user operating a plunger driver head assembly, in accordance with an embodiment of the disclosure.
Figure 13B:
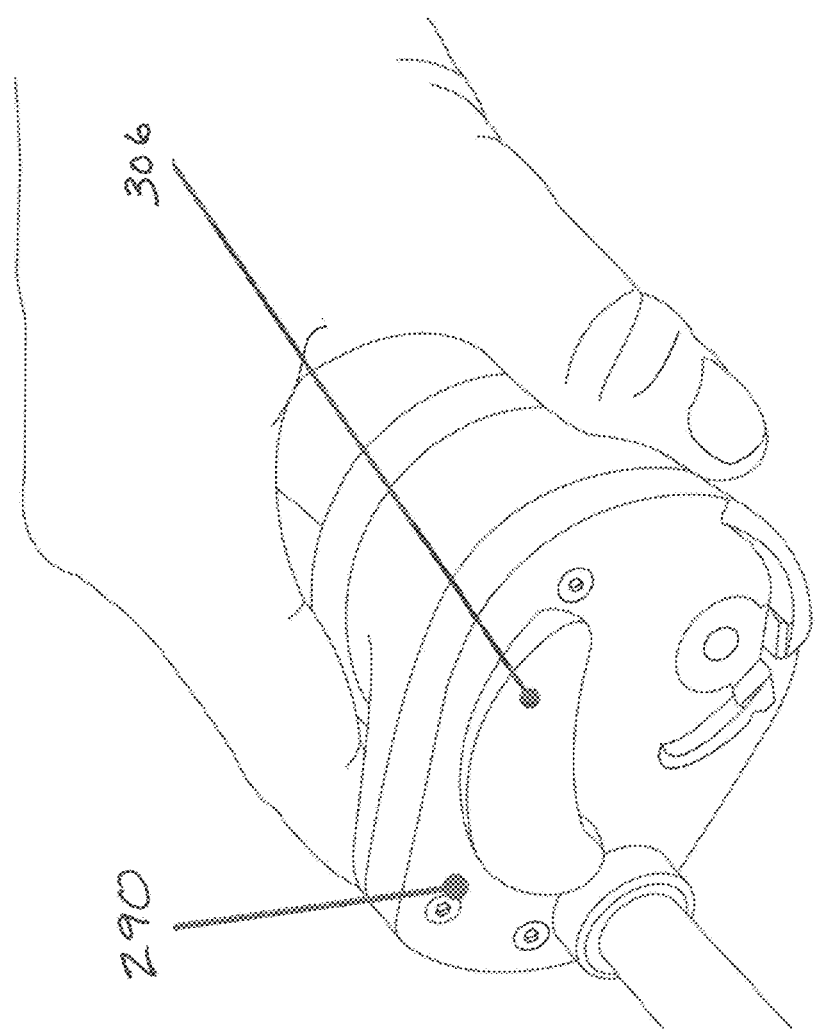
FIG. 13B is another perspective view of a user operating the plunger driver head assembly of FIG. 13A.

Referring now to FIGS. 13A-13B, in operation, the bumper 305, trigger 304, flipper 306, and barrel clamp lever 144 are used in loading and unloading operations of syringes into or out of the syringe receptacle 108. In the case of loading operations of syringes into the syringe pump 100, an initial step is to extend the plunger driver assembly 290 outwardly, away from the syringe receptacle 108. In order to accomplish this, a user can manipulate and engage the bumper 305 on the end of the plunger driver head assembly 294 using the palm of his/her hand while depressing the trigger 304 on the rear side of the plunger driver assembly 290 with his/her fingers of that same hand. Depressing the trigger 304 releases the plunger driver assembly 290 from its default position (i.e., the lead screw grip position) and enables the plunger driver assembly 290 to slide outwardly and away from the receptacle 108. Accordingly, the plunger driver assembly 290 is initially slid to a desired distance appropriate for the syringe barrel of the syringe to be loaded into the syringe receptacle 108.

Figure 14A:
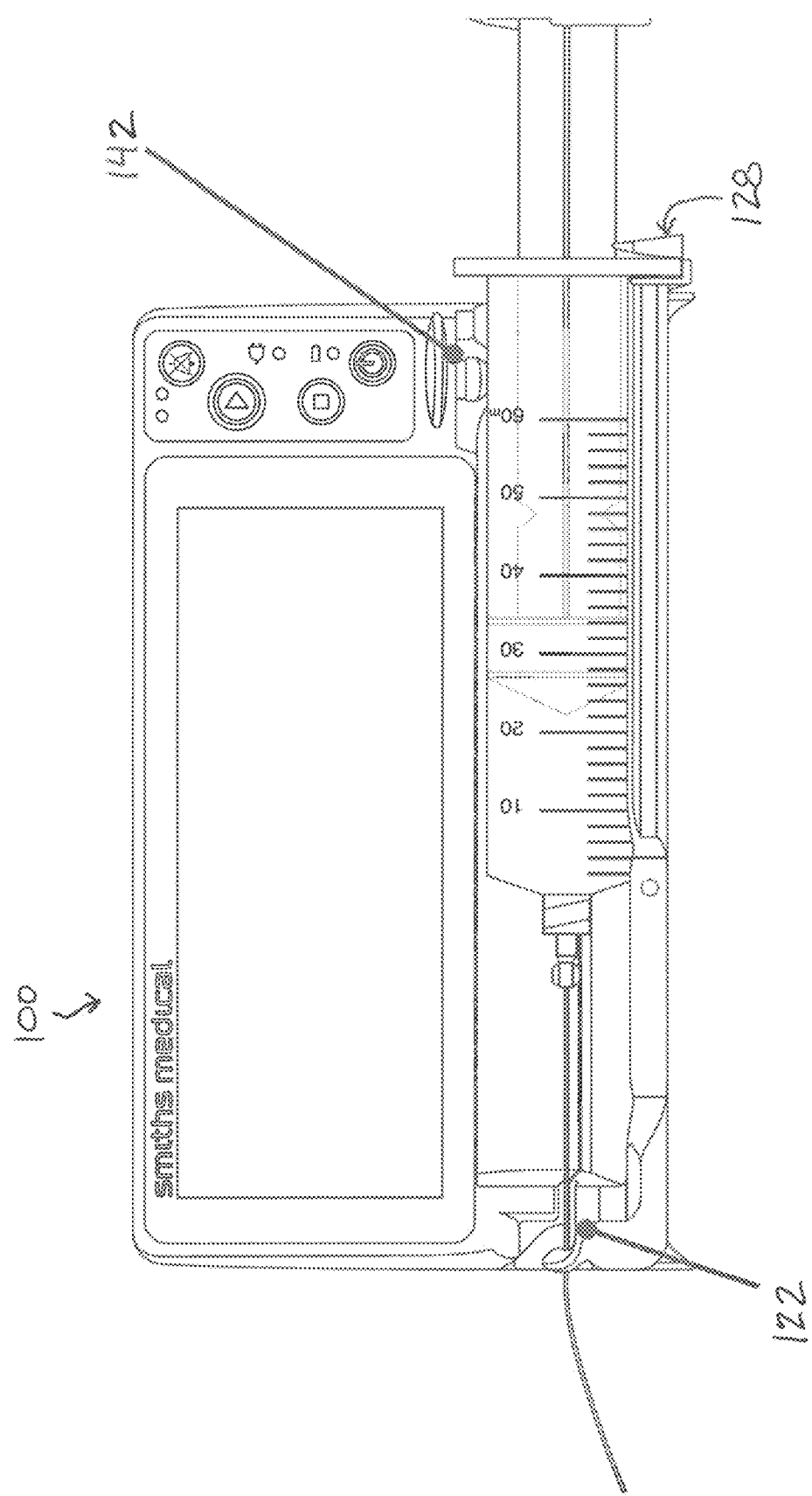
FIG. 14A is a front view of a syringe loaded into a syringe pump, in accordance with an embodiment of the disclosure.
Figure 14B:
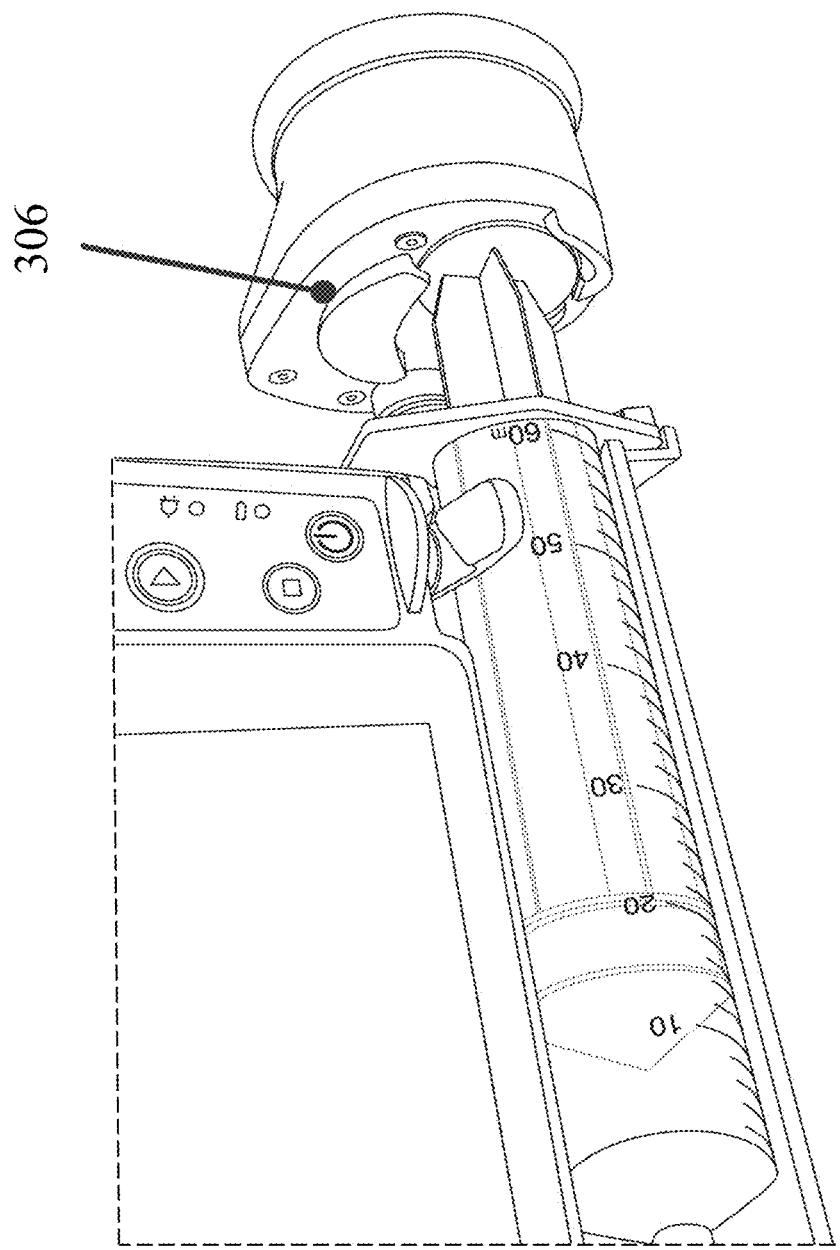
FIG. 14B is a partial front perspective view of FIG. 14A.

Referring now to FIGS. 14A-14B, next a syringe, which can be a syringe of a variety of shapes and sizes, is placed into the syringe receptacle 108, such that the end of the syringe barrel abuts the interior surface of the plunger driver assembly 290 location, opposite the bumper 304. An infusion line connected to the syringe is threaded through the retention passage 122 at the end of the syringe receptacle 108 located opposite the plunger driver assembly 290. When the trigger 304 is released, the flipper 306 rotates to descend over the thumb press of the plunger in the syringe barrel and the plunger driver assembly 290 is operably coupled to the lead screw 260. The barrel clamp lever 144 is manipulated so that the syringe barrel is further held in place. Accordingly, the barrel clamp lever 144 and trigger 304 configured to secure syringes of a variety of shapes and sizes within the syringe receptacle 108.

The user can then manipulate the user interface 104 to control the syringe pump 100 and the desired manner. The syringe drive assembly 106 can be responsible for controlling delivery of a prescribed amount or dose of an infusate from a syringe in the pump 100 to a patient by mechanically depressing a plunger in the syringe to deliver the infusate at a controlled rate through an infusion line fluidly connected to the syringe. More specifically, a motor 230 rotates the lead screw 260 which, in turn, causes the plunger driver head assembly 294 that is operably coupled to the lead screw 260 to move in a direction of the syringe receptacle 108. This movement then pushes the plunger within a barrel of the syringe located within the receptacle 108. Pushing the syringe plunger forward forces a dose of infusate in the syringe outwardly from the syringe, into the infusion line, and ultimately to a patient.

It should be understood that the individual steps used in the methods of the present teachings may be performed in any order and/or simultaneously, as long as the teaching remains operable. Furthermore, it should be understood that the apparatus and methods of the present teachings can include any number, or all, of the described embodiments, as long as the teaching remains operable.

Various embodiments of systems, devices, and methods have been described herein. These embodiments are given only by way of example and are not intended to limit the scope of the claimed subject matter. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed subject matter.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to an embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. For purposes of interpreting the claims, it is expressly intended that the provisions of 35 U.S.C. § 112 (f) are not to be invoked unless the specific terms "means for" or "step for" are recited in a claim.

The invention claimed is:

1. A syringe pump, comprising:
a housing;
a powertrain having a lead screw;
a clutch assembly including:
first and second half-nuts;
a cam having a first lobe and a second lobe, the first lobe operable to move the first and second half-nuts into engagement with the lead screw and the second lobe operable to move the first and second half-nuts into disengagement with the lead screw, wherein the first lobe is adjacent to the second lobe along a length of the cam; and
a leaf spring in communication with at least one of the first and second half-nuts; and
a plunger driver assembly including:
a flipper configured to be movable between a capture position and an open position;
a trigger connected to both the clutch assembly and the flipper; and
a biasing element configured to bias the flipper into the capture position.

2. The syringe pump of claim 1, wherein the plunger driver assembly is configured to enable one-handed operation during loading and unloading of a syringe into the syringe pump.

3. The syringe pump of claim 1, wherein the biasing element is further configured to bias the clutch assembly into engagement with the lead screw, and wherein the first lobe of the cam is arranged to cooperate with the biasing element of the plunger driver assembly to bias the clutch assembly into engagement with the lead screw.

4. The syringe pump of claim 1, wherein the plunger driver assembly further includes a bumper operably coupled to an outer portion of the syringe plunger driver assembly, the bumper being generally rounded in shape and fabricated of a resilient material configured to absorb external forces acting upon the plunger driver assembly to inhibit unintentional delivery of medicament as a result of an external force applied to the plunger driver assembly.

5. The syringe pump of claim 4, wherein the bumper is capable of absorbing a sustained force of up to five Newtons.

6. The syringe pump of claim 1, the powertrain further comprising a motor, wherein: with the clutch assembly engaged with the lead screw, the plunger driver assembly is movable by the motor; and
with the clutch assembly disengaged from the lead screw, the plunger driver assembly is manually movable by a user.

7. The syringe pump of claim 1, wherein depressing the trigger simultaneously shifts the clutch assembly into disengagement with the lead screw and the flipper to the open position.

8. The syringe pump of claim 1, further comprising a carriage assembly operably couplable to the lead screw and a drive train chassis, such that rotation of the lead screw forces the carriage assembly to translate relative to the drive train chassis, thereby translating the plunger driver assembly.

9. The syringe pump of claim 1, wherein the first lobe has a greater lift than the second lobe such that the clutch assembly is biased into engagement with the lead screw.

10. The syringe pump of claim 1, wherein the leaf spring is biased against the first lobe of the cam when the clutch assembly is engaged with the lead screw.

* * * * *